United States Patent [19]
Yan et al.

[11] Patent Number: 5,916,523
[45] Date of Patent: Jun. 29, 1999

[54] METHODS FOR NEAR SIMULTANEOUS CHEMILUMINESCENT SULFUR AND NITROGEN DETECTION

[75] Inventors: Xinwei Yan, Houston; Eugene Malcolm Fujinari, Spring, both of Tex.

[73] Assignee: Antek Instruments, Inc., Houston, Tex.

[21] Appl. No.: 08/760,247

[22] Filed: Dec. 4, 1996

[51] Int. Cl.⁶ .................................................. G01N 7/00
[52] U.S. Cl. ........................ 422/83; 422/52; 422/82.08; 73/23.2
[58] Field of Search .......................... 436/116–118, 119, 436/122, 123, 173; 422/83, 52, 82.07, 82.08, 91; 73/23.2

[56] References Cited

U.S. PATENT DOCUMENTS

| Re. 34,668 | 7/1994 | Parks et al. . | |
|---|---|---|---|
| 3,882,028 | 5/1975 | Zolner . | |
| 4,352,779 | 10/1982 | Parks . | |
| 4,678,756 | 7/1987 | Parks | 436/123 |
| 4,843,016 | 6/1989 | Fine | 436/116 |
| 5,227,135 | 7/1993 | Godec et al. | 422/98 |
| 5,310,683 | 5/1994 | Godec et al. | 436/123 |
| 5,330,714 | 7/1994 | Godec et al. . | |
| 5,424,217 | 6/1995 | Benner et al. . | |

FOREIGN PATENT DOCUMENTS 2163553  2/1986  United Kingdom .

OTHER PUBLICATIONS

Overheads of oral presentation: Simultaneous Selective Sulfur and Nitrogen Detection for Gas Chromatography (GC–CLSD/CLND) presented by Dr. Xinwei Yan, at the Advanced Laboratory Exposition and Conference, San Jose, California, Oct. 25, 1994.

H. Shi, J.T.B. Strode, III, L.T. Taylor, E.M. Fujinari, "Feasibility of Supercitical Fluid Chromatography–chemiluminescent Nitrogen Detection with Open Tubular Columns", *Journal of Chromatography*, 734 (1996) 303–310.

*Primary Examiner*—Lyle A. Alexander
*Attorney, Agent, or Firm*—Robert W. Strozier; J.M. Mark Gilbreth; Gilbreth & Strozier, P.C.

[57] ABSTRACT

A method and apparatus are disclosed for the near simultaneous detection of light emitted from ozone induced chemiluminescence of nitrogen and sulfur species capable of undergoing ozone induced chemiluminescence in a single instrument. A sample containing sulfur and/or nitrogen is first subjected to an oxidative/reductive process which generates ozone reactive nitrogen and sulfur species which are then forwarded to an specially designed ozone/detector chamber. The ozone reactive species are brought in contact with ozone in the special chamber and the chemiluminescence of the nitrogen species and the sulfur species are measured and quantitated.

14 Claims, 15 Drawing Sheets

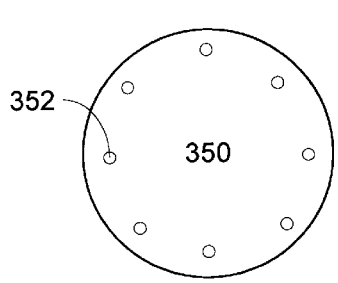
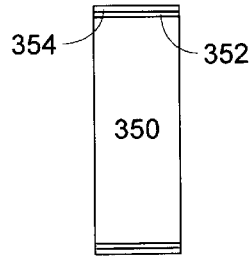
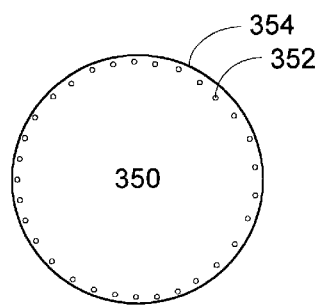
FIG. 4a   FIG. 4b   FIG. 4c
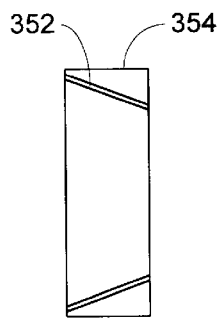
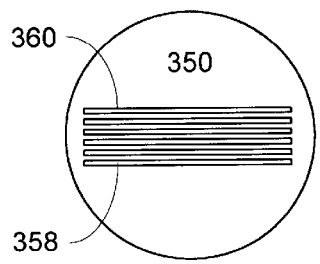
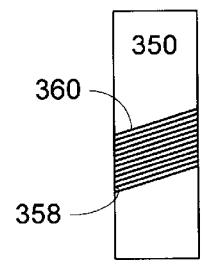
FIG. 4d   FIG. 4e   FIG. 4f
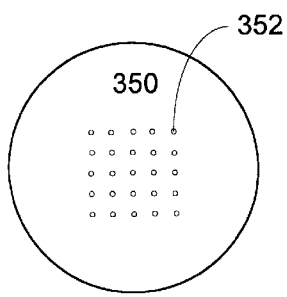
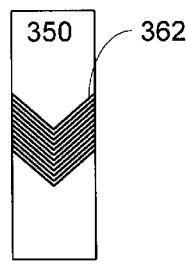
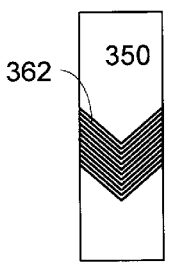
FIG. 4g   FIG. 4h   FIG. 4j
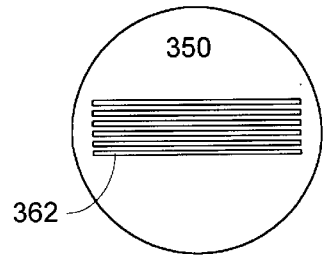
FIG. 4i

METHODS FOR NEAR SIMULTANEOUS CHEMILUMINESCENT SULFUR AND NITROGEN DETECTION

BACKGROUND OF THE INVENTION

1. Field of the Invention

This invention relates to a method and apparatus for the near simultaneous determination of sulfur and nitrogen in a sample material by a chemiluminescence detection and quantification technique.

More particularly, the present invention relates to a method and apparatus for the determination of nitrogen and sulfur in a sample material by oxidizing the sample material to generate nitrogen and sulfur oxides followed by reducing a portion of the sulfur oxides generating sulfur species capable of ozone induced chemiluminescence, while not reducing the nitrogen oxide species capable of ozone induced chemiluminescence, contacting the nitrogen and sulfur species with ozone to produce nitrogen chemiluminescent light and sulfur chemiluminescent light which lights are independently and substantially simultaneously detected and quantified.

2. Description of the Related Art

U.S. Pat. No. 4,018,562, now Re. 34,668 discloses a chemiluminescence technique for detecting and quantifying of nitrogen within a sample material. The sample material is first oxidized to convert the nitrogen in the sample into nitrogen oxides including nitric oxide. The nitric oxide is reacted with ozone to produce a chemiluminescent reaction. The emitted light energy is then detected in the 600–900 nanometer region of the electromagnetic spectrum. The intensity of this emitted light correlates to the quantity of nitrogen present in the original sample and measurement of this light by a photomultiplier tube or photodiode and associated circuitry permits one to quantify the amount of nitrogen present in the original sample.

U.S. Pat. No. 4,352,779 discloses a chemiluminescence techniques for detecting and quantifying sulfur within a sample. The sample material is first oxidized to convert the sulfur into oxides of sulfur. The oxides of sulfur are then subjected to a chemical reduction resulting in the formation of hydrogen sulfide that is reacted with ozone to produce a chemiluminescent reaction. The emitted light energy is then detected in the 300–500 nanometer region of the electromagnetic spectrum. The intensity of this emitted light or photoemission is measured by a photomultiplier tube or photodiode and associated circuitry generates a signal that correlates to the quantity of sulfur in the original sample.

Currently, chemiluminescence techniques are one of the most sensitive techniques with wide dynamic range for detecting and quantitating the concentration of nitrogen and/or sulfur in a sample material. These chemiluminescence devices are, however, nitrogen or sulfur specific and simultaneous determination of both sulfur and nitrogen require a dual analysis technique, i.e., the sample material is split into separate two fractions for separate nitrogen and sulfur detection. Sample fractionation procedures do not assure that each fraction has exactly the same composition. Moreover, if the sample to be analyzed is a chromatographically separated component of a more complex mixture of chemical components, the separated component may represent a very small amount of material making fractionation difficult and often times problematic. Thus, it would be an advancement in the all to have an apparatus and a method for near simultaneous detection of the concentration of nitrogen and sulfur in a sample by ozone induced chemiluminescence.

SUMMARY OF THE INVENTION

This invention provides a method for quantifying a nitrogen and sulfur content of a sample or portion thereof by ozone induced chemiluminescence. The method broadly includes converting a portion of the nitrogen and sulfur content of the sample in a heater or heated chamber in the presence of an oxidizing agent and a reducing agent into detectable concentrations of nitrogen species and sulfur species capable of undergoing ozone induced chemiluminescence. The partially converted sample is then contacted with ozone in a reaction/detection chamber including a nitrogen chemiluminescence detector and a sulfur chemiluminescence detector. The ozone activated nitrogen and sulfur species then chemiluminesce, the light of which is detected in the reaction/detection chamber so that the nitrogen chemiluminescent light does not substantially interference with detecting the sulfur chemiluminescent light and the sulfur chemiluminescent light does not substantially interfere with detecting the nitrogen chemiluminescent light.

The method converts the sample by oxidizing the sample in the presence of an oxidizing agent to convert a portion of the nitrogen and a portion of the sulfur in the sample to oxides of nitrogen and oxides of sulfur. The resulting oxidized sample containing the oxides of nitrogen and oxides of sulfur is then reduced in the presence of a reducing agent to convert a portion of the sulfur oxides into sulfur species capable of undergoing ozone induced chemiluminescence without reducing the nitrogen oxide species capable of undergoing ozone induce chemiluminescence below a detectable level.

The resulting reduced sample containing the nitrogen and sulfur species capable of undergoing ozone induced chemiluminescence are reacted with ozone to generate metastable nitrogen and sulfur species that chemiluminesce in a light bifurcated ozone reaction chamber including a nitrogen chemiluminescence detection zone and a sulfur chemiluminescence detection zone separated by a gas permeable, light barrier. The nitrogen chemiluminescence is measured using a nitrogen photo-detection system associated with the nitrogen detection zone and the sulfur chemiluminescence is measured using a sulfur photo-detection system associated with the sulfur detection zone. The resulting measurements are then related back to the nitrogen and sulfur content in the sample.

The present invention also provides an apparatus for determining the concentration of nitrogen and sulfur in a sample or a portion thereof, by ozone induced chemiluminescence. The apparatus includes a furnace system having an oxidizing zone where an oxidizing agent converts a portion of the nitrogen and sulfur in the sample into nitrogen oxides and sulfur oxides and a reducing zone where a reducing agent converts a portion of the sulfur oxides into reduced sulfur species capable of undergoing ozone induced chemiluminescence without concurrently reducing the nitrogen oxide species capable of ozone induced chemiluminescence below a detectable level.

Next, the reduced sample containing the ozone reactive nitrogen and sulfur species is forwarded to a light bifurcated, ozone reaction and chemiluminescence detection chamber by a transfer conduit. The conduit is designed to transfer the sample exiting the furnace system to the chamber. The apparatus also includes a device to suppress water vapor condensation so that a water vapor concentration in the sample does not condense in the transfer conduit or chamber after exiting the furnace. The condensation suppression device is generally a vacuum system which also help to forward or pull the sample into and through the transfer conduit and the chamber at a sufficient flow rate to allow efficient analysis of the sample or sample components and to maintain a pressure in the chamber below a given pressure of generally 50 Torr.

Once the sample enters the chamber, the sample is then reacted with ozone in a nitrogen detection sub-chamber having an associated nitrogen chemiluminescence detection system the an ozone induced nitrogen chemiluminescence is measured by the nitrogen detection system. The ozone-sulfur species reaction products in the sample are then forwarded through a gas permeable, light barrier to a sulfur detection sub-chamber having an associated sulfur chemiluminescence detection system where an ozone induced sulfur chemiluminescence is measured by the sulfur detection system. The detected nitrogen chemiluminescent light and sulfur chemiluminescent light are then related to the nitrogen and sulfur content in the sample in a signal analyzer that relates the detected light to the concentration of nitrogen and sulfur in the sample.

Each detection system associated with the sub-chambers includes a window, an optical filter, a photo-detector and associated electronics and signal processing hardware and software. The nitrogen sub-chamber includes an ozone and a sample entry port. The sample and ozone are mixed in the nitrogen sub-chamber where the nitrogen detecting system detects the instantaneous chemiluminescence of the meta-stable nitrogen dioxide thought to be formed from the ozone oxidation of nitric oxide. In addition to the oxidation of nitric oxide, the reduced sulfur species react with ozone to produce meta-stable sulfur dioxide. The ozone oxidized sample containing the meta-stable sulfur species is then forwarded to the sulfur sub-chamber through a gas transfer device that allows the detection of the meta-stable sulfur species, but substantially inhibits the propagation of light between the chambers, where the sulfur detection system detects the sulfur chemiluminescence.

DESCRIPTION OF THE DRAWINGS

The invention can be better understood with reference to the following detailed description together with the appended drawings where like elements are numbered the same:

FIGS. 4a–b are a front and cross-sectional view of a first embodiment of the gas permeable, light barrier of FIG. 1;

FIGS. 4c–d are a front and cross-sectional view of a second embodiment of the gas permeable, light barrier of FIG. 1;

FIGS. 4e–f are a front and cross-sectional view of a third embodiment of the gas permeable, light barrier of FIG. 1;

FIGS. 4g–h are a front and cross-sectional view of a forth embodiment of the gas permeable, light barrier of FIG. 1;

FIGS. 4i–j are a front and cross-sectional view of a fifth embodiment of the gas permeable, light barrier of FIG. 1;

DESCRIPTION OF THE PREFERRED EMBODIMENTS

Figure 1:
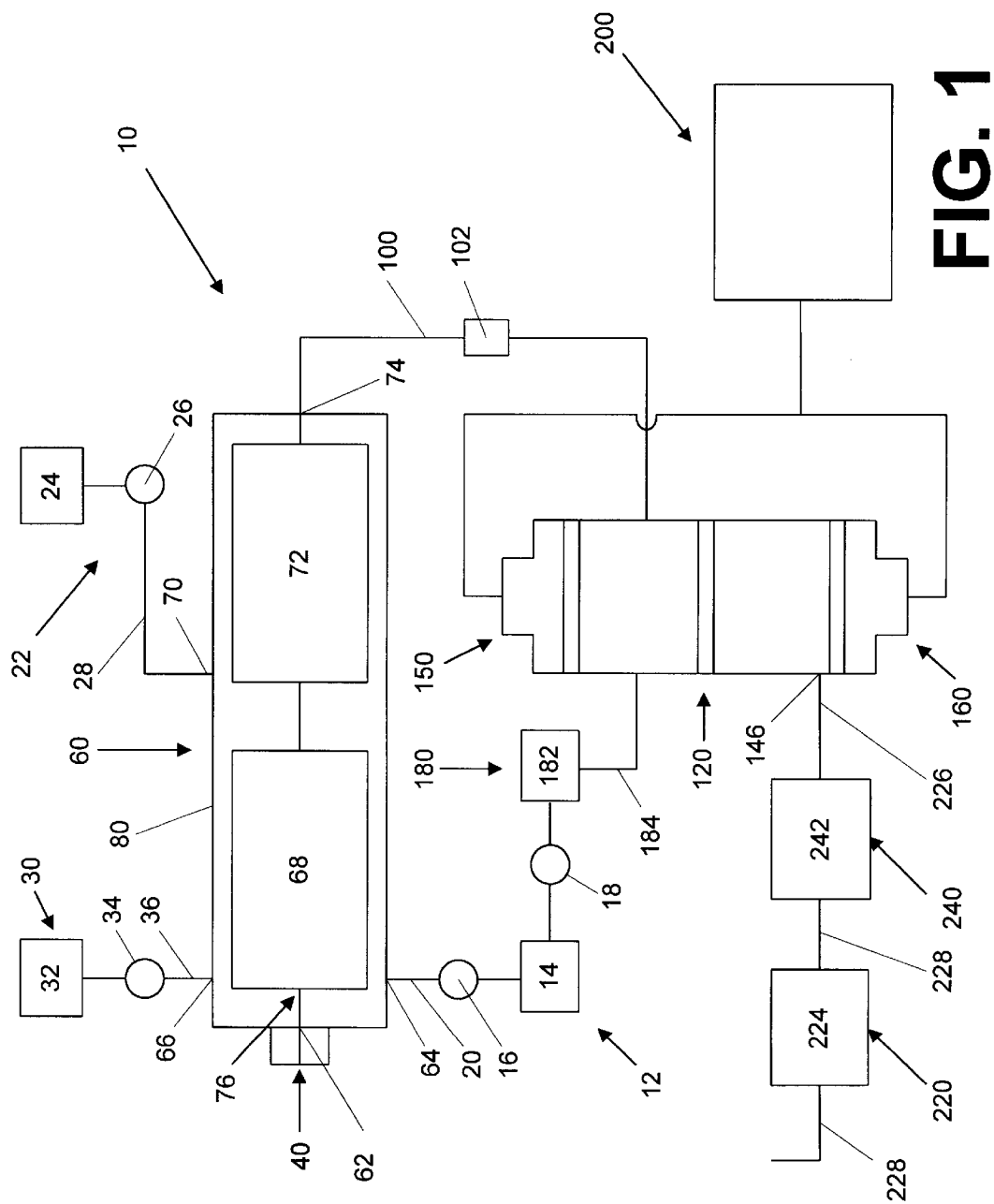
FIG. 1 is an electrical and mechanical schematic drawing of a chemiluminescent detection apparatus for the simultaneous measurement and quantitation of the concentration of nitrogen and sulfur in a sample material.

The inventors have found that a method and an apparatus can be designed that is capable of near simultaneous determination of a concentration of nitrogen and sulfur in a sample or portion thereof using ozone induce chemiluminescence within a light partitioned detection chamber. The ability to measure both nitrogen and sulfur in a single device comes from the realization that a sample can be subjected to sequential oxidation and reduction to generate nitrogen and sulfur species capable of undergoing ozone induced chemiluminescence in sufficient concentrations to be nearly simultaneously and independently detectable by a nitrogen detection system and a sulfur detection system. The nitrogen detection system is associated with a first sub-chamber of the light partitioned chamber, while the sulfur detection system is associated with a second sub-chamber separated from the first sub-chamber by a gas permeable, light barrier.

Moreover, the inventors have found that the chemiluminescence of the nitrogen species capable of undergoing ozone induced chemiluminescence occurs at a much faster rate than the chemiluminescence of the sulfur species so that the nitrogen chemiluminescence can be independently detected without substantial interference from the sulfur chemiluminescence and vis-a-versa. The term without substantial interference means with the same nitrogen and sulfur concentration in a sample that less than about 10% of the signal detected by the nitrogen detection system is derived from sulfur chemiluminescence and vis-a-versa, preferably, less than about 5% of the signal detected by the nitrogen detection system is derived from sulfur chemiluminescence and vis-a-versa, particularly, less than about 2% of the signal detected by the nitrogen detection system is derived from sulfur chemiluminescence and vis-a-versa, and especially, less than about 1% of the signal detected by the nitrogen detection system is derived from sulfur chemiluminescence and vis-a-versa.

For many purposes it is desirable to know, quantify and/or quantitate the concentration of both nitrogen and sulfur in a sample, including nitrogen and sulfur chemically bound in organic, inorganic, bio-inorganic or bio-organic materials, e.g., quantitation of nitrogen and sulfur contents of proteins, organics, refinery streams or the concentrations in potential sulfur and nitrogen pollutants, such as nitrogen oxides and sulfur oxides, in fuels or fuel exhaust gases. Moreover, the concentration of nitrogen and/or sulfur in a sample or component thereof can assist in characterizing the samples and/or components thereof. Such characterization may be desirable in monitoring feed stocks for use in catalytic conversions or other chemical processes which are generally sensitive to the concentration of nitrogen and/or sulfur in the feed stock.

The method of this invention includes oxidizing a sample at elevated temperature in the presence of an oxidizing agent to convert a portion of the nitrogen and sulfur in the sample to oxides of nitrogen including nitrogen species capable of undergoing ozone induced chemiluminescence, and oxides of sulfur. The oxidized sample, containing the oxides of nitrogen and oxides of sulfur, as well as oxides of carbon and, other oxides including water vapor, is then reduced at elevated temperature in the presence of a reducing agent to convert a portion of the oxides of sulfur into a detectable amount of sulfur species capable of undergoing ozone induced chemiluminescence without reducing the nitrogen species capable of undergoing ozone induce chemiluminescence below a detection limit.

The reduced sample, containing both detectable quantities of the ozone reactive nitrogen and sulfur species is then reacted with ozone to generate meta-stable nitrogen and sulfur species that chemiluminesce in a light bifurcated detection chamber. The resulting chemiluminescent light or photoemission of the meta-stable nitrogen and sulfur species is then separately detected in the light bifurcated detection chamber using nitrogen and sulfur specific photo-detection systems.

Generally, the light bifurcated detection chamber is a single evacuated, light tight chamber which is partitioned into two sub-chambers or zones where the sub-chambers or zones are separated by an gas permeable, light barrier. The barrier generally is perforated where the perforations are preferably not straight and/or are near the outer edge with the barrier. However, the detection chamber can also include two sub-chambers connected by tubing preferably coiled or bent so that light can not propagate from one sub-chamber to the other sub-chamber. Moreover, if the barrier is a bent or coiled tube, then the inner surface of the tube is preferably coated with a non-reflective, light absorbing coating. It should be recognized that the light barrier is gas permeable and designed to reduce light generated from one sub-chamber or zone from propagating into the other sub-chamber or zone.

This invention also relates to an effluent including detectable concentrations of nitrogen species and sulfur species capable of undergoing ozone induced chemiluminescence resulting from first oxidizing the sample in the presence of an oxidizing agent to produce detectable concentrations of nitrogen oxides capable of undergoing ozone induced chemiluminescence and sulfur oxides. The oxidized sample is then reduced in the presence of a reducing agent to reduce the sulfur oxides to sulfur species capable of undergoing ozone induced chemiluminescence without concurrently reducing the nitrogen oxides capable of ozone induced chemiluminescence below a detectable level of the nitrogen chemiluminescence detection system. It should be recognized by ordinary artisans that certain sulfur oxides, such as sulfur monoxide (SO), are also capable of undergoing ozone induced chemiluminescence and are likely formed during oxidation. However, there is considerable debate in the scientific community as to whether the SO formed during oxidation survives reduction. Moreover, any SO formed during reduction may also not survive long enough to be independently measured in the reaction chamber after it reacts with ozone and chemiluminesces. Irrespective of the debate over SO, the present invention only requires the formation and detection of detectable concentrations of sulfur species capable of undergoing ozone induced chemiluminescence.

The apparatus and method of the invention will be jointly described in more detail herein. The description will set forth the mode of operation and will specify the arrangement of apparatus necessary to carry out the present invention. In the process and by the apparatus of this invention, a solid, liquid, and/or gaseous sample can be analyzed to determine the concentration of both sulfur and nitrogen in the sample in a near simultaneous detection of ozone induced chemiluminescence of nitrogen and sulfur species.

Suitable oxidizing agents for use in this invention include purified oxygen gas, air, or other oxygen gas mixtures. Suitable reducing agents for use in this invention include hydrogen, hydrogen containing gases, or other reducing gases.

The oxidation and reduction of the sample are generally carried out in a particulated, ceramic tube. However, non-particulated tube such as metal and quartz tubes can also be used, but the efficiency of the conversion and analysis may be somewhat diminished. The tubes suitable for use in the furnace system of the present invention can be any material capable of withstanding temperatures up to about 2000° C.

Although many materials are suitable for such uses, the preferred materials include, silicas, aluminas, zirconias, silica-aluminas, alumina-silicates, other high temperature ceramics, or mixture or combinations thereof. The particularly preferred materials include highly purified alumina tubes and zirconia tubes. These tubes are highly particulated, i.e., the tubes have considerable surface roughness. The oxidation and reduction is thought to be facilitated to some extent by the surface which may act both as a catalytically active oxidizing and reducing surface. Additionally, the tubes can be surface treated with specific catalytically active materials to enhance oxidation and/or reduction. Such catalytically active materials include transition metal oxides as well as other catalytic species.

Although the sample is preferably burned and reduced in a two stage process, it is possible to simultaneously burn and reduce the sample in a single stage. One such process would involve combusting the sample in a reducing flame or flame front. Thus, a single furnace could be used where the sample, oxygen and hydrogen are all combined and the mixture ignited. By carefully controlling the sample, hydrogen and oxygen ratios, a reducing flame or flame front can be maintained such that detectable amounts of nitric oxide and reduced sulfur species are produced for subsequent chemiluminescent detection. Such furnace assemblies as well as other furnace assemblies useable in this invention are disclosed for example in U.S. Pat. Nos.: 4,352,779; 4,678,756; 5,227,135; 5,310,683; 5,330,714; and 5,424,217, incorporated herein by reference.

General Details of the Apparatus

Referring now to FIG. 1, an apparatus, generally 10 for practicing the process of this invention includes, in its most general parts: (1) an oxygen containing gas supply assembly 12 having an oxygen tank 14, a first and second oxygen flow controller 16 and 18 and associated flow lines 20; (2) a hydrogen containing gas supply assembly 22 having hydrogen tank 24, a hydrogen flow controller 26 and associated flow lines 28; and (3) a carrier gas supply assembly 30 having a carrier gas tank 32, a carrier gas flow controller 34 and associated flow lines 36. These three assemblies 12,22, 30 separately carry and meter their respective gases to their various points of utilization in the apparatus.

The apparatus 10 also includes a sample introduction assembly 40, a furnace assembly or heated chamber 60 for oxidizing and reducing a sample to produce measurable quantities of nitrogen and sulfur species capable of undergoing ozone induced chemiluminescence, a transfer conduit 100 for forwarding the furnace assembly effluent to a light bifurcated chamber 120 which has associated therewith a nitrogen chemiluminescent light detection system or detector 150 which detects ozone induced chemiluminescence of the nitrogen species and a sulfur chemiluminescent light detection system or detector 160 which detects ozone induced chemiluminescence of the sulfur species, an ozone generator assembly 180 for generating ozone and supplying the ozone to the chamber 120, a signal analyzer 200 in electronic communication with the detection systems 150 and 160 that converts the detector signals into quantitative nitrogen and sulfur concentrations, a device 220 to suppress water vapor condensation in the transfer conduit 100 and in the chamber 120, and optionally an ozone scrubber 240 to scrub the effluent from the chamber 120 to remove unreacted ozone. The conduit 100 can, and preferably does, have a restrictor 102 associate therewith. The restrictor 102 restricts the flow of gases from the heated chamber 60 so that when the device 220 is a vacuum system, the pressure in the chamber 120 can be maintained at a desirable low pressure, generally, below about 50 Torr.

Sample Introduction, Oxidation, and Reduction

A sample can be introduced through the sample introduction assembly 40 to the furnace assembly 60 in a variety of ways. A liquid or gas sample can be directly injected into the furnace assembly 60 through an injection port having a septum. The injection port has associated therewith a carrier gas inlet which helps to carry the sample into the furnace assembly 60. For a solid sample, the sample can be analyzed in its gas form by vaporization (heat induced) or sublimation (heat or vacuum induced) or dissolved in a suitable liquid carrier and then injected or otherwise introduced into the furnace assembly 60 into a carrier gas. These techniques are all well known in the art of analytical chemistry.

Alternatively, the sample introduction assembly 40 can be a simple interface between any sample separation instrument where the separation instrument outlet is connected to the inlet 40 of the furnace assembly 60. Suitable instruments include, without limitation, gas chromatographs (GC), high performance liquid chromatographs (HPLC), liquid chromatographs (LC), and other similar separation instruments. Moreover, the sample introduction assembly 40 can also be simply a valve operated line from a continuous source of a material to be analyzed such as a refinery stream or the like.

Broadly speaking, the furnace assembly 60 includes a sample inlet 62, an oxygen inlet 64, an optional carrier gas inlet 66, an oxidation zone 68, a hydrogen inlet 70, a reduction zone 72, and a sample outlet 74.

The sample enters the furnace assembly 60 through the sample inlet 62 where the sample is combined or contacted with an amount of an oxygen containing gas from the oxygen inlet 64 which is connected to the oxygen supply assembly 12 and optionally with a carrier gas from the carrier gas inlet 66 which is connected to the carrier gas supply assembly 30 in a mixing zone 76 which can be a first portion 78 of the oxidation zone 68. The oxygen containing gas is metered through the first flow controller 16 to the oxygen inlet 64, while the carrier gas, if used, is metered through the flow controller 34 to the carrier gas inlet 66.

The sample is then oxidized in the presence of an effective amount of oxygen containing gas to oxidize, and preferably completely oxidize, the sample converting a portion, preferably all, of the nitrogen and sulfur in the sample into nitrogen oxides and sulfur oxides as the sample proceeds from the mixing zone 76 through the oxidation zone 68. The oxidation is not so robust to oxidize dinitrogen, but is robust enough to oxide most other nitrogen containing compounds and most, if not all, sulfur containing compounds include elemental sulfur. Preferably, the flow rate of oxygen and the sample material through the zone 68 is set to establish a residence time within the zone 68 sufficient to completely oxidize of the sample.

Typically, the carrier gas is an inert gas, but this is not always the case. In certain separation techniques such as gas chromatography (GC), the carrier gas could be hydrogen which is, of course, not an inert gas. When the apparatus supplies a carrier gas directly from supply assembly 30, then the flow rate of the gas is controlled by the controller 34. Where a sample is in the nature of a gas or liquid directly injected into the furnace assembly 60, a flow rate of the carrier gas of about 1 to about 100 cubic centimeters per minute is generally used to help oxidation and reduction efficiencies. The flow rate of the carrier gas should be sufficient to ensure proper operation of the apparatus 10.

The oxidation reaction directly converts a portion (preferably all) of the nitrogen containing compounds in the sample into nitrogen oxides including nitrogen oxides capable of undergoing ozone induced chemiluminescence such as nitric oxide. Additionally, the oxidation reaction directly converts a portion (preferably all) of the sulfur compounds into sulfur oxides including some capable of undergoing ozone induced chemiluminescence such as sulfur monoxide. However, due to the extreme reactivity of sulfur monoxide, this sulfur oxide is likely quantitatively converted into other sulfur oxides. Of course, the oxygen also oxidizes any carbon containing components into carbon oxides and converts the hydrogen in the sample into water.

The oxidation zone 68 is typically maintained at an elevated temperature to increase the rate of oxidation and reduce the required residence time in the zone 68 and to ensure that detectable quantities of nitrogen and sulfur oxides are produced. Generally, the temperature range is between about 300° C. to about 2200° C., preferably between about 600° C. to about 1700° C., and particularly between about 800° C. to about 1200° C. Because it is desirable to have complete or near complete oxidation of the sample, the oxygen from oxygen assembly 12 is metered through the controller 16 into the oxidation zone 68 through the oxygen inlet 64 in an amount in excess of the amount stoichiometrically necessary to oxidize the oxidizable components in the sample.

Since it is often difficult to determine the concentration of oxidizable components in a sample, prior to introduction into the furnace system 60, the amount of oxygen containing gas metered into the oxidation zone 68 will generally be between about 2 to about 6 times higher than the amount of carrier gas metered into the oxidation zone either directly from the assembly 30 or contained in the sample, if the sample is derived from a separation instrument such as a GC. It should be recognized that the combustion which occurs in the furnace system 60 must be robust enough to oxidize all carbon compounds to components that will not form unsaturated hydrocarbons that are capable of ozone induced chemiluminescence.

The oxidized sample material from oxidization zone 68, next passes to the reduction zone 72 where the oxidized sample is contacted with a hydrogen containing gas from the hydrogen gas supply assembly 22, the flow into the reduction zone 72 of which is controlled by the controller 26. The hydrogen flow rate into reduction zone 72 is an amount sufficient to ensure a hydrogen rich atmosphere within the reduction zone 72 of the furnace assembly 60. The reduction zone 72 is generally maintained at an elevated temperature, typically in the range between about 300° C. and about 2200° C., and preferably between about 600° C. and about 1700° C.

The temperature and hydrogen flow rate are controlled so that a portion, and preferably all, of the sulfur oxides present in the oxidized sample are converted to reduced sulfur species capable of undergoing ozone induced chemiluminescence. Reduced sulfur species known to undergo ozone induced chemiluminescence include, without limitation, hydrogen sulfide, sulfur, sulfur monoxide, polysulfides, $H_xS_y$ species or other sulfur species capable of undergoing ozone induced chemiluminescence. However, the reduction condition cannot be so robust as to reduce the amount of nitrogen oxides capable of undergoing ozone induced chemiluminescence below a detection limit of the nitrogen detection system. The nitrogen oxides capable of ozone induced chemiluminescence include predominantly nitric oxide. Thus, a detectable amount of nitric oxide that may be present in the oxidized sample passing to the reduction zone must not be reduced by the hydrogen rich environment below the detection limit for the nitrogen detection system for nitric oxide.

The oxygen or oxygen containing gas and the hydrogen or hydrogen containing gas flow rates are generally maintained to a certain ratio of hydrogen to oxygen in the furnace assembly 60. The ratio of $H_2:O_2$ is generally between about 55:1 and about 8:1, with the preferred ratio being between about 35:1 and about 15:1 and the particularly preferred ratio being between about 30:1 and about 20:1. The hydrogen flow rate are generally between about 350 mL/min and about 125 mL/min, with rates of between about 320 mL/min and about 150 being preferred and rates between about 175 mL/min to about 160 mL/min being particularly preferred. The oxygen flow rate is generally between about 30 mL/min and about 1 mL/min, with rates between about 25 mL/min and about 5 mL/min being preferred and rates between about 22 mL/min and about 6 mL/min being particularly preferred. However, higher and lower flow rates can be used provided that the $H_2:O_2$ ratio is maintained. The carrier gas flow rate can be any flow rate that allows the oxidation and reduction reaction to proceed efficiently.

The oxygen supplied to the furnace assembly should be sufficient to oxidize the entire amount of combustible material in the sample into oxides. Generally, the amount of sample introduced into the furnace will be from about 2 μL to about 0.1 μL, preferably from about 1.5 μL to about 0.15 μL and particularly, from about 1 μL to about 0.2 μL.

Often the sample introduction assembly 40 will also include a splitter to reduce the amount of sample entering the furnace assembly 60 as is well known in the art. The splitter is used generally with light hydrocarbon samples and is generally not used with heavy or complex hydrocarbon samples.

Figure 2A:
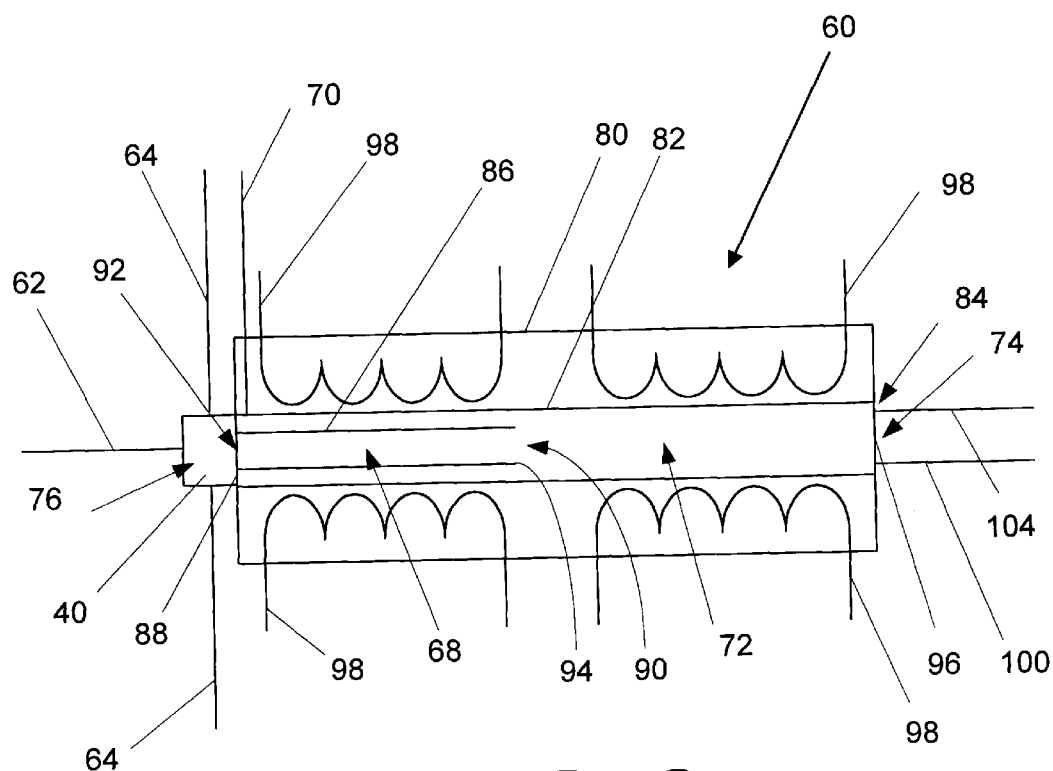
FIG. 2a is a first embodiment of the furnace system of FIG. 1.

Referring to FIG. 2a, a first embodiment and the preferred embodiment of the furnace assembly 60 is shown in greater detail. The furnace assembly 60 includes a housing 80, a larger outer ceramic tube 82 extending the length of the housing 80 through a central region 84 thereof and a smaller inner ceramic tube 86 inserted inside the outer tube 82 and extending from a first end 88 of the outer tube 82 to near a middle region 90 thereof. The sample, oxygen, and optional carrier gas enter a first end 92 of the inner tube 86 the length of which constitutes the oxidation zone 68. The oxidized sample exits a second end 94 of the inner tube 86 and enters the outer tube 82 the remaining length of which constitutes the reduction zone 72 where the oxidized sample is contacted with hydrogen gas supplied through the hydrogen inlet 70. The reduced sample then exits the outer tube 82 through a second end 96 of the outer tube 82 which is associated with the sample outlet 74.

The furnace assembly 60 also includes a heating element 98 associated with the oxidation zone 68 and the reduction zone 72. Preferably, the heating element 98 include more windings associated with the oxidation zone 68 which provides for a higher temperature in the oxidation zone than in the reduction zone. Alternatively, the furnace can have two independently controllable elements, one associated with the oxidation zone and one associated with the reduction zone where the temperature in the two zones 68 and 72 can be maintained at the same or different temperature similar to the arrangement shown in FIG. 2b.

Figure 2B:
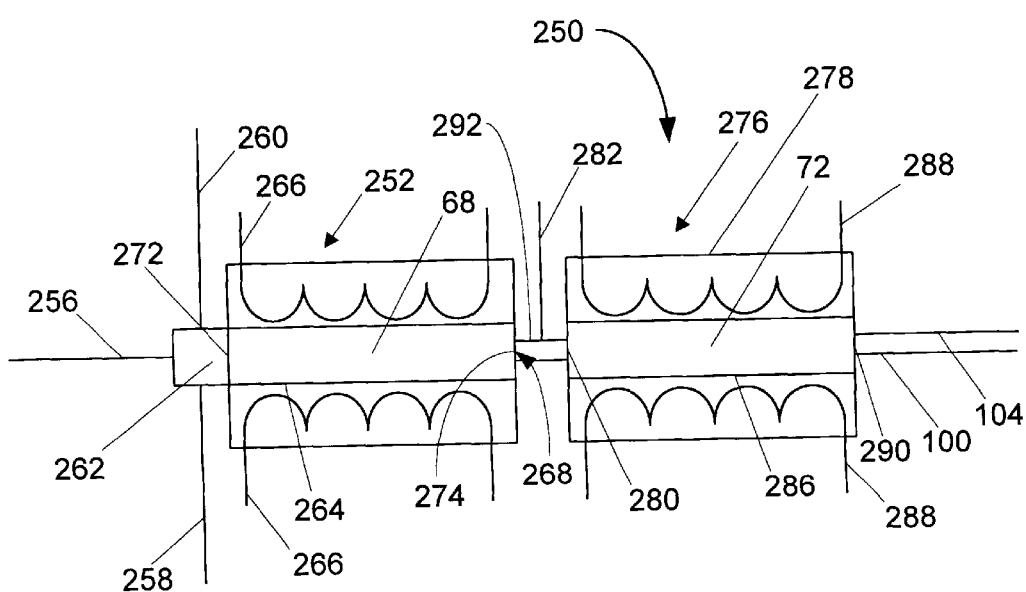
FIG. 2b is a second embodiment of the furnace system of FIG. 1.

Referring now to FIG. 2b, a second embodiment of a furnace assembly 250 can be seen to include a first furnace 252 having a housing 254, a sample inlet 256, an oxygen inlet 258, and a carrier gas inlet 260 (for the optional introduction of a carrier gas). The first furnace 252 also includes a mixing zone 262 (which again can be a first portion of the oxidation zone 68), a quartz or ceramic or pyrobysto tube 264, a heating element 266, and a sample outlet 268. The tube 264 extends down a central region 270 of the housing 254 of the first furnace 252 from a first end 272 to a second end 274 thereof.

The furnace assembly 250 also includes a second furnace 276 having a housing 278, a sample inlet 280, a hydrogen inlet 282, a mixing zone 284 which can be a first portion of the reduction zone 72, a ceramic tube 286, a heating element 288 and a sample outlet 290. The sample outlet 268 of the first furnace 252 is connected to the sample inlet 280 of the second furnace 276 by a transfer line 292, while the sample outlet 290 of the second furnace 276 is connected to the transfer conduit 100. The hydrogen inlet 282 can be associated with the transfer line 292 and the transfer line 292 can also have a sample vent (not shown) associate therewith up stream of the hydrogen inlet 282 for reducing the overall amount of sample being passed to the second or reduction furnace 276. The vent is generally used when analyzing samples that have large amount of hydrocarbon species, such as a refinery stream or a natural gas stream.

Ozone Induced Chemiluminescence and Detection

Figure 3A:
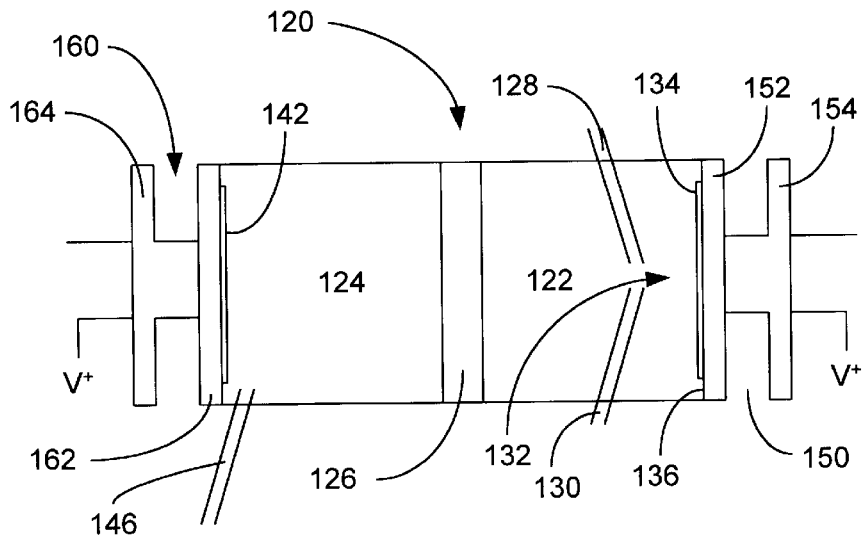
FIG. 3a is an expanded view of a first embodiment of the ozone/detection chamber of FIG. 1.

The sample exiting the furnace assembly 60 or 250 is next forwarded via the transfer conduit 100 to the light bifurcated chamber 120 where the sample is contacted with ozone producing meta-stable nitrogen and sulfur species that chemiluminesce and are separately detected. With reference to FIG. 3a, the chamber 120 in a first preferred embodiment, includes a first sub-chamber 122, a second sub-chamber 124 and a gas permeable, light barrier 126 separating the sub-chambers 122 and 124. The first sub-chamber 122 includes a sample inlet tube 128 which is connected to conduit 100 and an ozone inlet tube 130 which in connected to the ozone supply line 184.

The ozone is supplied to the ozone inlet tube 130 from an ozone generator assembly 180, where the assembly 180 includes an ozone generator 182 to produce ozone from the oxygen or oxygen containing gas supplied by the oxygen assembly 12 through the controller 18. The ozone rich gas is communicated to the ozone inlet tube 130 of the sub-chamber 122 via an ozone delivery line 184.

The sample inlet tube 128 and the ozone inlet tube 130 direct the sample and the ozone into a central region 132 of the sub-chamber 122 directly in front of a first light transparent port 134 in a first end 136 of the sub-chamber 122. The ozone reaction products include the meta-stable nitrogen species which substantially chemiluminesces in the sub-chamber 122. The emitted light passes through the port 134 and is detected by the nitrogen chemiluminescent detection system 150 which includes an optical filter 152 which passes light having a wavelength range between about 600 nm and about 2200 nm and a detector 154 for detecting light having a wavelength range between about 650 nm and about 900 nm. The light detector 154 can be a photo-multiplier tube or a photo-diode or any other photo-detecting device provided the device can quantitate the number of photons emitted between about 650 nm and about 900 nm. Because the chemiluminescence of sulfur species is much slower than the chemiluminescence of nitrogen species, only a small fraction of sulfur chemiluminescence occurs in the first sub-chamber during the sample's residence time in the first sub-chamber. Moreover, the optical filter 152 further reducing sulfur interference in the nitrogen detection system because sulfur chemiluminesces between about 300 nm and about 500 nm.

After die ozone and the sample are combined in the central region 132 of the first sub-chamber 122, the ozone activated sample including the activated sulfur species are then forwarded through the gas permeable, light barrier 126 located at a second end 138 of the first sub-chamber 122 to a first end 140 of the second sub-chamber 124. The second sub-chamber 124 includes a port 142 at a second end 144 of the sub-chamber 124 opposite the barrier 126 and a sample outlet 146. The port 142 has associated therewith a sulfur chemiluminescence detection system 160 which includes a second optical filter 162 which passes light having a wave length between about 250 nm and about 500 nm and a detector 164 for detecting light of that wavelength range. The light detector 164 can be a photo-multiplier tube or a photo-diode or any other photo-detecting device provided the device can quantitate the number of photons emitted between about 300 nm and about 500 nm. Because the nitrogen chemiluminescence is much faster than the sulfur chemiluminescence, little nitrogen chemiluminescence interferes with the sulfur chemiluminescence and the filter 162 further reduces any nitrogen chemiluminescent interference.

The nitrogen and sulfur species capable of undergoing ozone induced chemiluminescence react with ozone producing meta-stable nitrogen and other species. The predominant nitrogen species that reacts with ozone is thought to be nitric oxide (NO) and reactions with ozone to produce electronically excited nitrogen dioxide which chemiluminesces according to Equation 1:

$$NO + O_3 \rightarrow NO_2^* \rightarrow NO_2 + h\nu \qquad (1)$$

The light emitted in equation 1 is in the wave length range between about 600 nm and about 2200 nm and the reaction is very fast.

The sulfur species capable of ozone induced chemiluminescence include hydrogen sulfide, sulfur monoxide (an extremely short lived chemical species), and other sulfur species (SS) capable of undergoing ozone induced chemiluminescence. The sulfur species, SS, are thought to react with ozone to form electronically excited sulfur dioxide which chemiluminesces according to Equation 2:

$$SS + O_3 \rightarrow SO_2^* \rightarrow SO_2 + h\nu \qquad (2)$$

It is thought that sulfur monoxide is actually an immediate precursor of the electronically excited sulfur dioxide according to Equation 3:

$$SO + O_3 \rightarrow SO_2^* \qquad (3)$$

That is, it is thought that SS first reacts with ozone to form SO which then reacts with ozone to generate electronically excited $SO_2$ which then chemiluminesces. Whatever the pathway to the excited sulfur dioxide, the reaction of the sulfur species with ozone to generate chemiluminescent light is much slower than the chemiluminescent reaction of nitric oxide with ozone.

Figure 3B:
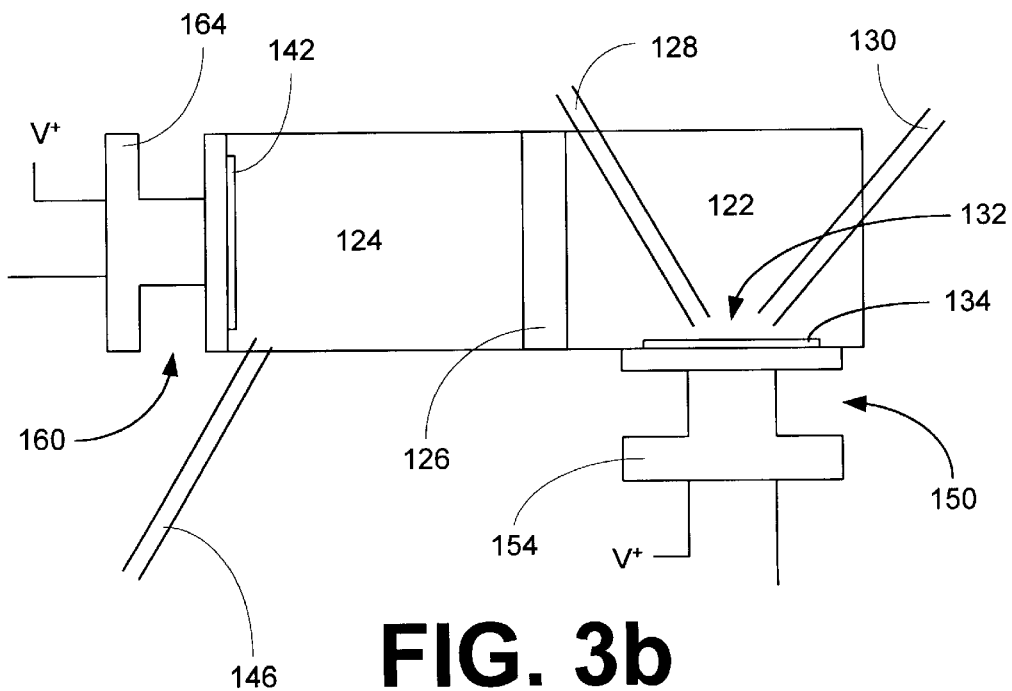
FIG. 3b is an expanded view of a second embodiment of the ozone/detection chamber of FIG. 1.
Figure 3C:
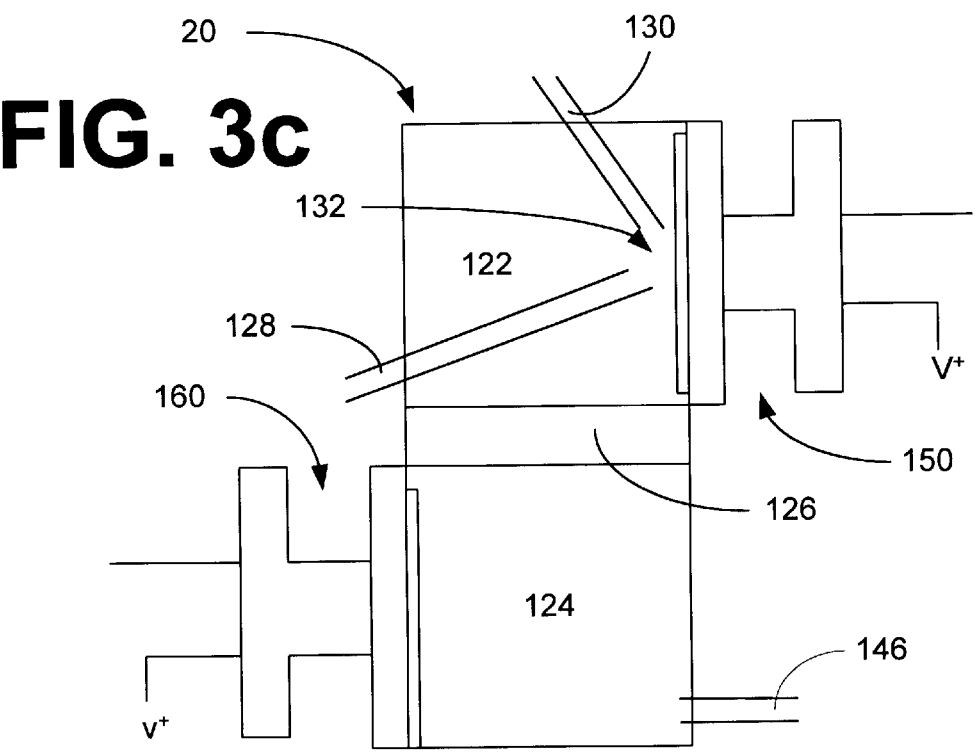
FIG. 3c is an expanded view of a third embodiment of the ozone/detection chamber of FIG. 1.
Figure 3D:
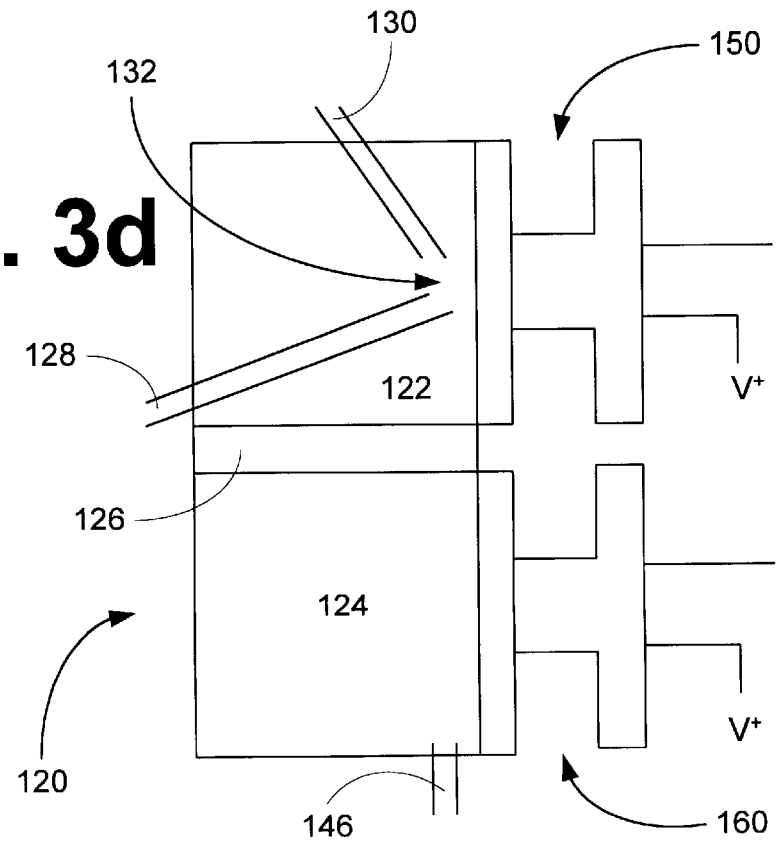
FIG. 3d is an expanded view of a forth embodiment of the ozone/detection chamber of FIG. 1.

Referring now to FIG. 3b, a second embodiment of the partitioned chamber 120 is shown which has the nitrogen detection system 150 and the sulfur detection system 160 aligned perpendicular to each other. Again, the light barrier 126 separates the chamber into two sub-chambers. In FIG. 3c, another embodiment of the partitioned chamber 120 is shown which has the nitrogen and sulfur detection systems on opposite sides of the chamber 120 to form a S-shaped chamber/detector system. While in FIG. 3d, the chamber 120 and nitrogen and sulfur detection systems form a U-shaped chamber/detector system.

Although the preferred embodiments of the bifurcated chamber 120 includes a disk shaped, air permeable, light barrier 126 other chamber assemblies can be used as well. For example, the sub-chambers could be connected by a piece of light absorbing bent tubing (the tubing has a interior coating that absorbs light or at least does not reflect light). Because nitrogen chemiluminescence is much faster than sulfur chemiluminescence, the preferred design of the bifurcated chamber 120 is to have the first sub-chamber 122 smaller than the second sub-chamber 124. This preferred design is such that the sub-chamber 122 is about ½ the size of the second sub-chamber 124 and particularly about ¼ the size of the second sub-chamber 124. Optimally, the sub-chamber 122 can be designed so that at a given sample and ozone flow rate, substantially all of the nitrogen chemiluminescence occurs in the first sub-chamber 122 and preferably just in front of the port 134 and substantially all of the sulfur chemiluminescence occurs in the second sub-chamber 124.

Figure 3E:
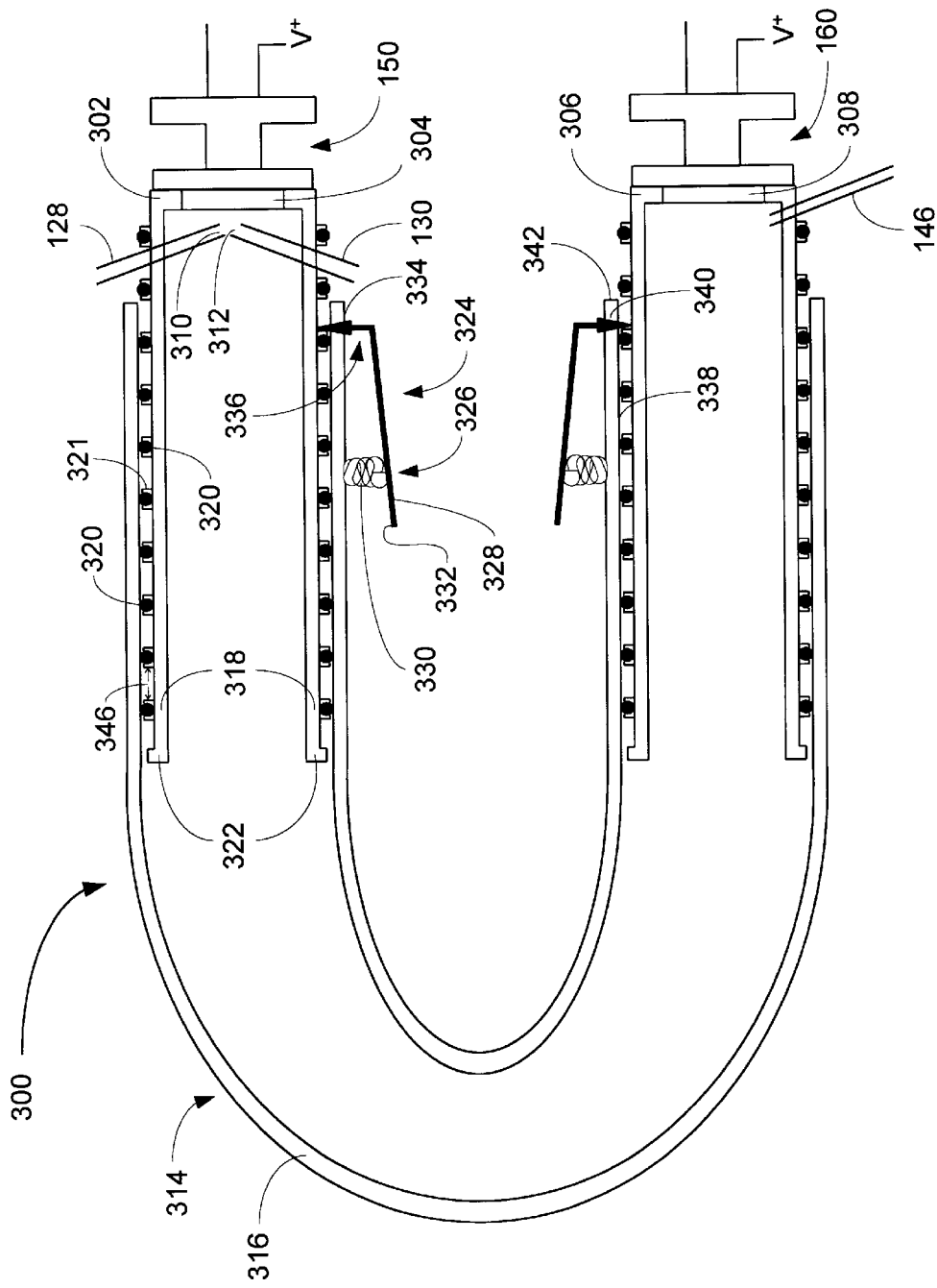
FIG. 3e is an expanded view of a fifth embodiment of the ozone/detection chamber of FIG. 1.

Alternatively, the chamber 120 can be tunable. One embodiment of a tunable chamber 120 comprises an adjustable, U-shaped chamber 300 with the nitrogen detector 150 located at a first end 302 having a first transparent port 304 and with the sulfur detector 160 located at a second end 306 having a second transparent port 308 as shown in FIG. 3e. The sample enters the chamber 300 through the sample inlet 128 and the ozone enters the chamber 300 through the ozone inlet 130. The sample and ozone inlet exits 310 and 312 are centered in front of the first port 304 so that the ozone-sample mixing occurs in right in front of the first port 304. The inlets 128 and 130 are preferably angled toward the port 304 to maximize the nitrogen chemiluminescence directly in front of the port 304 so that a substantial portion of the nitrogen chemiluminescent light passes into the nitrogen detector 150. The preference for angled sample and ozone inlets is the same for all embodiments of the chamber of the present invention.

The inventors have found that the ozone induced nitrogen chemiluminescence is kinetically faster than the ozone induced sulfur chemiluminescence. When this fact is coupled with a vacuum pump attached to the sample outlet 146 as the device for inhibiting water condensation in the apparatus, then the sample residence time near the port 304 is relatively short resulting in the nitrogen detector 150 be able to detect nitrogen chemiluminescence substantially free of sulfur chemiluminescence interference.

As the ozone activated sample is pulled by the vacuum pump toward the outlet 146 associated with the other end of the chamber 300, the nitrogen chemiluminescence begins to die out and the sulfur chemiluminescence begins to build up. By adjusting a sample travel path distance, i.e., the curvilinear distance between the first end 302 and the second end 306, at a given sample and ozone flow rate and at a given pump rate of the vacuum pump, the chamber 300 can be tuned to maximize the nitrogen and sulfur responses detected by the nitrogen and sulfur detector 150 and 160, respectively, and to minimize interference from sulfur chemiluminescence in the nitrogen detector 150 and nitrogen chemiluminescence in the sulfur detector 160. The ozone flow rate is maintained between about 10 mL/min and about 50 mL/min, preferably between about 15 mL/min and about 40 mL/min, and particularly between about 20 mL/min and about 30 mL/min.

The travel path adjusting device 314 can be any device that moves the ends further from each other. In FIG. 3e, one embodiment of the device 314 includes a sliding U-shaped middle member 316 of the chamber 300 that acts like the slide of a trombone, and two straight members 318 which slidingly engage the middle member 316. The middle member 316 is shown here as sliding on a series of O-rings 320 affixed to the straight members 318 by housing 321. The O-rings 320 ensure that the engagement between the middle member 316 and the straight end members 318 is sufficient to maintain a light tight and vacuum tight condition in the chamber 300. The device 314 also includes two stop members 322 also associated with the two straight end member 318 and two retractably locking devices 324 that lock the slide member 316 in place.

The locking devices 324 are shown here as two finger operated, spring loaded locking device 326 including an arm 328 having a spring 330 associated with a first end 332 and a locking member 334 associated with a second end 336. The locking member 334 is designed to extend below an interior surface 338 of the slide member 316 through a slot 340 therein located near two ends 342 of the slide member 316 when the arm 328 is in a locked condition. By depressing the end 332 toward an other surface 344 of the slide member 316, the locking member 334 associated with the second end 336 of the arm 328 can be retracted from the slot 340. When both locking devices 324 are in a retracted condition (pressure being applied by a user's hand), the slide member 316 can be moved in or out to tune the instrument. A distance 346 between the O-rings 320 is generally between about 0.25 cm and about 3 cm, preferably between about 0.5 cm to about 2.5 cm and particularly between about 0.5 cm and about 2 cm. Although other spacings can be used as well.

The embodiment of the chamber 300 shown in FIG. 3e does not require a light barrier 126, but one can be used if desired. Moreover, when using a light barrier, the chamber 300 can be straight. Furthermore, the exact shape of the chamber 300 is not critical provided that the shape inhibits light generated near the port 304 from propagating to the port 308 and vis-a-versa.

Light Barriers

The gas permeable, light barrier 126 can comprise any device that allows the ozone reacted product to proceed from the first sub-chamber 122 to the second sub-chamber 124 in a manner so that light emitted in the first sub-chamber does not directly propagate to the second sub-chamber and vis-a-versa, i.e., sulfur chemiluminescence is not substantially detected in the first sub-chamber and nitrogen chemiluminescence is not substantially detected in the second sub-chamber. Suitable barrier devices include perforated disks, bent tubes, baffles, porous materials dividers, or the like.

Referring to FIGS. 4a–j, five examples of barrier devices 126 suitable for use in the apparatus of the present invention are shown, for convenience the bifurcated chamber 120 is generally a cylindrical chamber so that the barriers 126 are disk shaped. Of course, the chamber 120 can be of any shape such as rectangular, triangular, oval, or any other geometrical solid shape; provided, however, that the chamber 120 and the sub-chambers or zones 122 and 124 are light tight and capable of holding a vacuum of less than 50 Torr.

Referring now to FIGS. 4a–b, the barrier 126 is shown as a disk 350 having a plurality of perforations 352 located near an outer edge 354 of the disk 350. The perforations 352 are straight as shown in FIG. 4b. Although the perforation channels 352 are straight and may allow some light to propagate between the two sub-chambers 122 and 124, the location of the perforations 352 near the outer edge 354 of the disk 350 reduces the impact this light would have on the detector because the ports 134 and 142 extend over only a portion of the area of the wall of the chamber to which the ports are associated.

Preferably, as shown in FIGS. 4c–d, the barrier 126 includes a disk 350 having a plurality of perforations 352 located near an outer edge 354 of the disk 350 where the perforation 352 are angled as shown in FIG. 4d so that light propagation directly between the two sub-chambers 122 and 124 is reduced because the light would likely come into contact with a wall 356 of the perforations 352. Of course, the perforations 352 do not have to be angled exactly as shown in FIG. 4b and generally are angled at a sufficient angle so that light cannot propagate from one sub-chamber to the other. Such an angle will generally be between about 5° and about 70°, with an angle between about 15° and about 60° being preferred.

In FIGS. 4e–f, an other barrier disk 350 is shown to include a plurality of angled slots 358 that extend through the disk and are angled so that light cannot propagate between the two sub-chambers without contacting a wall 360 of the slots 358 Yet, another barrier disk 350 is shown in FIGS. 4g–h including a plurality of perforations 352 that form V-shaped channels through the disk 350. Still another disk 350 is shown in FIGS. 4i–j including a plurality of angled slots 362 that form V-shape channels. All of these embodiments of the light barrier 126 are gas permeable yet prevents an interfering quantity of light to pass from the first sub-chamber to the second sub-chamber of the light partitioned chamber and visa-versa.

Alternately, the barrier 126 can be made of porous or fretted materials which are permeable to gases, but inhibits light from propagating through the porous material because the light will contact a portion of the surface making up the porous material. For this type of barrier 126, porous plastics, ceramics or metal are preferred. However, any porous material that does not cause the deactivation of the excited sulfur dioxide can be used as well; provided, of course, that the material is opaque to light between about 50 nm and about 3000 nm to substantially reduce interference between the detection nitrogen and sulfur chemiluminescence in each sub-zone of the chamber 120.

The light detected by the detection systems 150 and 160 is quantified in the circuitry of a signal analyzer 200 which is in electronic communication with the detection system 150 and 160 and converts the signals from the nitrogen and sulfur detectors into quantitative nitrogen and sulfur concentrations. The signal analyzer 200 converts the current signals from the photomultipliers or photodiodes detectors to voltage based signals which are then amplified in the analyzer 200 and related to the concentration of sulfur or nitrogen in the sample or sample component. The output signal from the analyzer 200 can then be displayed or recorded on various types of recording or display devices.

After the sample exits the furnace system 60, the sample, which has been oxidized and then reduced, generally contains a relatively large concentration of water vapor, and the water vapor can condense on cool surfaces after exiting the furnace system 60 and entering the transfer conduit 100. The transfer conduit 100 is generally made of a flexible material and may have an inert lining 104 (see FIGS. 2a and 2b) made preferably of a fluorinated polymer like Teflon. Preferably the conduit 100 is made out of a polymeric material that does not reaction with or absorb the nitrogen and sulfur species traveling through it. Such polymeric materials include, without limitation, fluorinated polymers such as Telfon, polyolefins such as polyethylene, polypropylene, PVC, or other similar polymeric or plastic materials.

The conduit 100 preferably also has a restrictor 120 associated therewith that restricts the flow of gases to the chamber 120 so that a pressure below about 50 Torr can be maintained in the chamber 120. Preferably, the pressure in the chamber is maintained below about 30 Torr and particularly, the pressure in the chamber is maintained below about 20 Torr, and especially the pressure in the chamber is maintained below about 5 Torr. The preferred operating range for the chamber 120 is between about 5 Torr and about 25 Torr. The lower the pressure in the chamber, the better the signal because less quenching of the excited molecules occurs via collisional deactivation. The detectable limits of the nitrogen system is generally greater than about 0.1 ppb (part per billion) and preferably greater than about 0.5 ppb.

To prevent the water vapor formed during the combustion process from condensing on cool surfaces, the apparatus 10 includes a device 220 for preventing the condensation of water vapor. The preferred water condensation prevention device 220 is a vacuum system 222 having a vacuum pump 224, a vacuum line 226 connected to the outlet 146 and an exhaust line 228. The vacuum system 222 reduces the pressure in the transfer conduit 100 and the chamber 120 and thereby preventing the condensation of water vapor as the sample is pulled by a vacuum through the transfer conduit 100 into the chamber 120 and out the outlet 146.

The vacuum system 222 and the restrictor 102 control the flow rate of the sample from the furnace system 60 to the chamber 120 through the transfer conduit 100. Although the preferred water condensation preventing device 220 is a vacuum system, drying systems can also be used to remove water vapor from the sample after it leaves the furnace system 60 and before the sample enters the chamber 120. However, the drying system must not cause the loss of nitrogen or sulfur species. Many conventional drying agents are not suitable because conventional drying systems typically use a desiccant which can absorb or adsorb sulfur and/or nitrogen species. Moreover, even if a dyer is used, a vacuum system is also used to reduce the pressure in the chamber 120 to maintain a pressure in the chamber 120 below about 50 Torr.

The apparatus 10 can optionally include a scrubber 240 for scrubbing the effluent from the chamber 120 to remove unreacted ozone prior to the effluent entering the device 220 to ensure that the ozone does not damage the device 220. The scrubber 240 includes an ozone scrubber 242 connected to the outlet 146 via a line 244 where the scrubber 242 is designed to destroy any unreacted ozone and generally, includes a solid material such as Hopcalite® catalysts available from Callery Chemical Company of Pittsburgh, Pa.

The apparatus 10 is generally calibrated before use by adjusting the operation conditions such as the flow rates of the carrier gas, reducing agent (hydrogen containing gas), oxidizing agent (oxygen containing gas), and ozone gas as well as the temperature in the oxidation and reduction zones for a particular standard sample. Upon calibration using a standard containing a known content of nitrogen and sulfur (generally bound in an organic molecular structure), the electronics of the apparatus may be set to provide a direct readout of the quantity of nitrogen and/or sulfur detected by the apparatus.

The apparatus and method of this invention are particularly well suited to serve as a detector and quantification device used in association with other instrumentation, such as gas and liquid chromatographs or other sample separation instrumentation. Where the sample comes from a gas chromatograph, a separate carrier gas is generally not needed because the sample coming from the gas chromatograph generally already is in the presence of a carrier gas as it enters the apparatus 10.

EXAMPLES

The following examples illustrate the usefulness of the present invention in the near simultaneous detection of nitrogen chemiluminescence and sulfur chemiluminescence in a single device. The sample feed was taken from a Varian Model 3400 GC using a 1 $\mu$L splitless injection. The GC was equipped with a capillary column having a SPB-1 (Supelco) stationary phase, a dimension of 30 m×0.32 mm ID and a film thickness of 4 $\mu$m. The GC was temperature programmed from 100° C. to 300° C. at 25° C./min for nitrogen and sulfur standard samples, from 40° C. to 200° C. at 4° C./min for gasoline samples and from 10° C. to 320° C. at 4° C./min with a 5 minute hold at 320° C. for diesel fuel and middle distillate samples.

After the sample components exited the GC, a portion of each component was feed into the furnace assembly 60 for oxidative and reductive treatment of the apparatus of the present invention and the resulting sample was analyzed in the nitrogen chemiluminescence detector (CLND) and the sulfur chemiluminescence detector (CLSD). A portion of each component was also forwarded to the flame ionization detector (FID) associated with the GC so that the FID response could be compared to the CLND and CLSD responses.

Two sulfur and two nitrogen compounds were used as standards for the purpose of calibrating the response of the apparatus 10. Tables 1–3 show the physical properties, the dilution series run, and the relative response factors, respectively, of the standards.

TABLE 1

Physical Properties of the Sulfur and Nitrogen Standards

| Compound | Molecular Weight (g/mole) | Boiling Point (°C.) | % S | % N |
| --- | --- | --- | --- | --- |
| 2-Ethylthiophene | 112.19 | 132–134 | 25.58 | — |
| Thianaphthene | 134.20 | 221–222 | 23.89 | — |
| Indole | 117.15 | 253 | — | 11.96 |
| 3-Methylindole | 131.18 | 265–266 | — | 10.68 |

TABLE II

S/N Concentrations (in ppm) and Dilutions ration of S/N Standards

| Compound | Sample S/N Concentrations | | | Sample Dilution Ratios | | |
| --- | --- | --- | --- | --- | --- | --- |
| | #1 | #2 | #3 | #1 | #2 | #3 |
| 2-Ethylthiophene | 271 | 54.3 | 10.68 | 2.17 | 0.434 | 0.087 |
| Thianaphthene | 256 | 51.3 | 10.25 | 2.05 | 0.410 | 0.082 |
| Indole | 249 | 49.8 | 9.95 | 1.99 | 0.398 | 0.080 |
| 3-Methylindole | 249 | 49.8 | 9.95 | 1.99 | 0.398 | 0.080 |

TABLE 3

Relative Response Factors for the Standards

| Compound | Sample Relative Response Factors | | |
| --- | --- | --- | --- |
| | #1 | #2 | #3 |
| 2-Ethylthiophene | 1.08 | 1.09 | 0.98 |
| Thianaphthene | 1.00 | 1.05 | 0.94 |
| Indole | 1.00 | 0.99 | 1.00 |
| 3-Methylindole | 1.00 | 1.00 | 0.98 |

Figure 5:
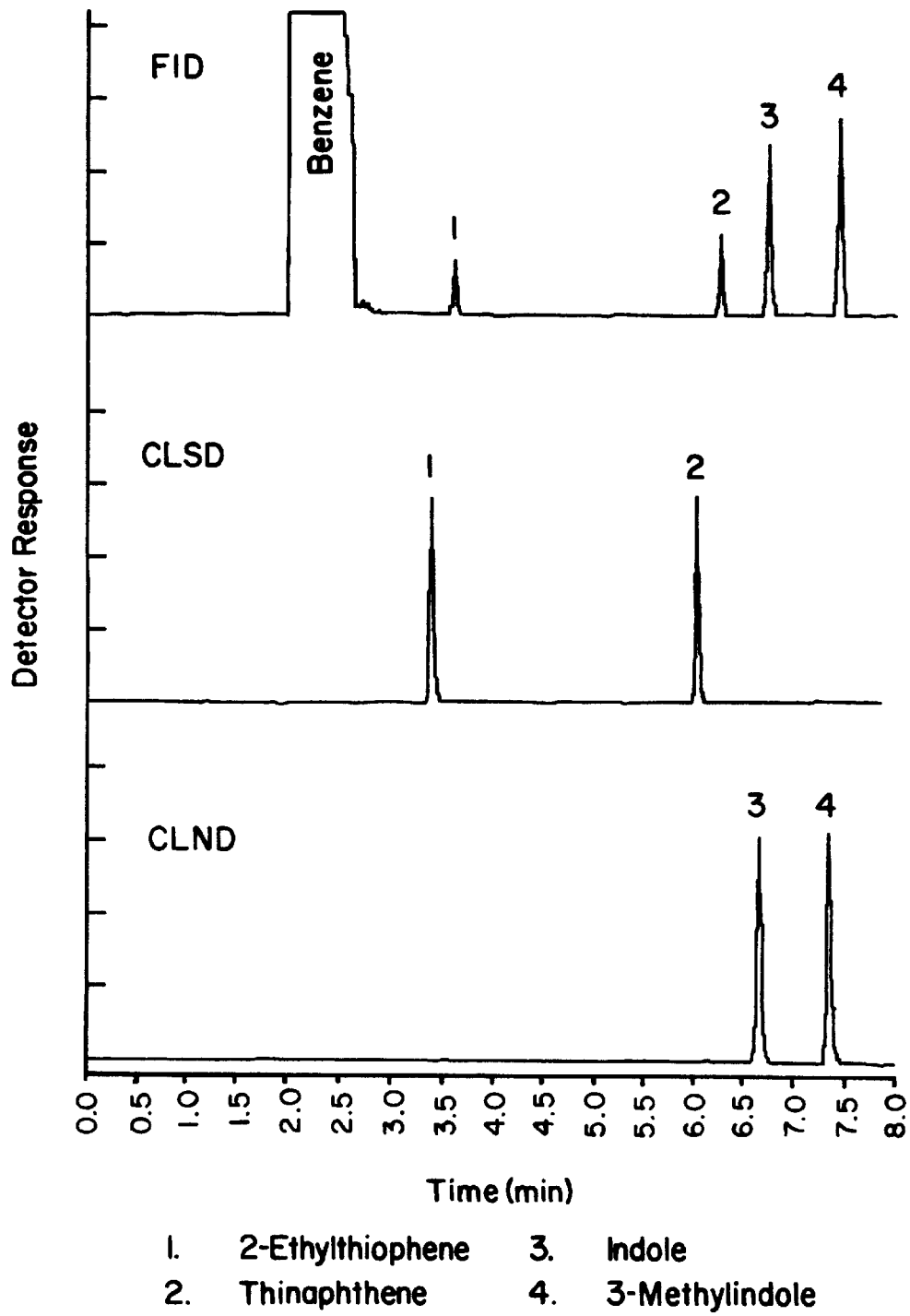
FIG. 5 is a set of simultaneous chromatograms of 250 ppm sulfur and 250 ppm nitrogen calibration standards.
Figure 6:
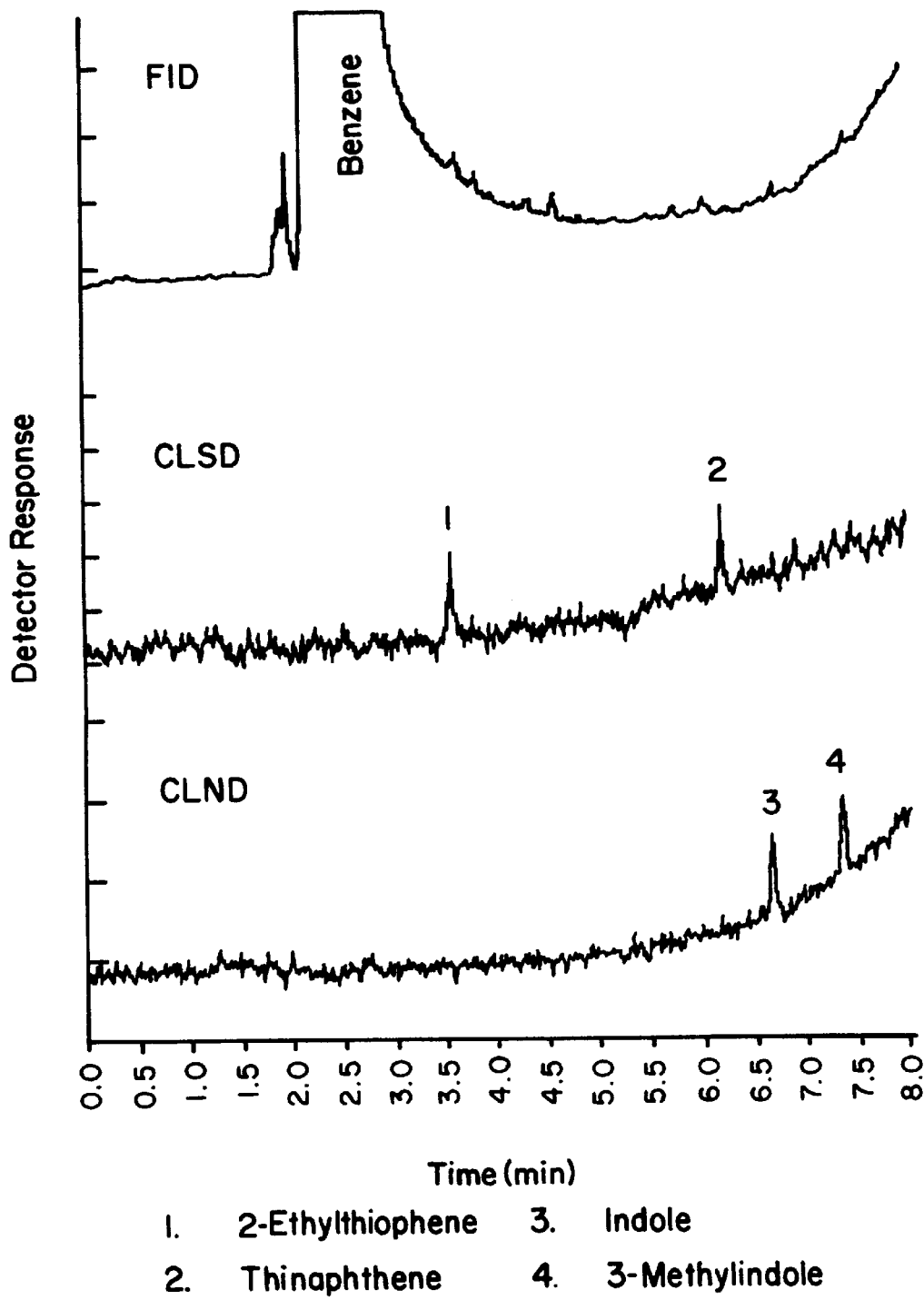
FIG. 6 is a set of simultaneous chromatograms of 125 pg sulfur and 125 pg nitrogen calibration standards.
Figure 7:
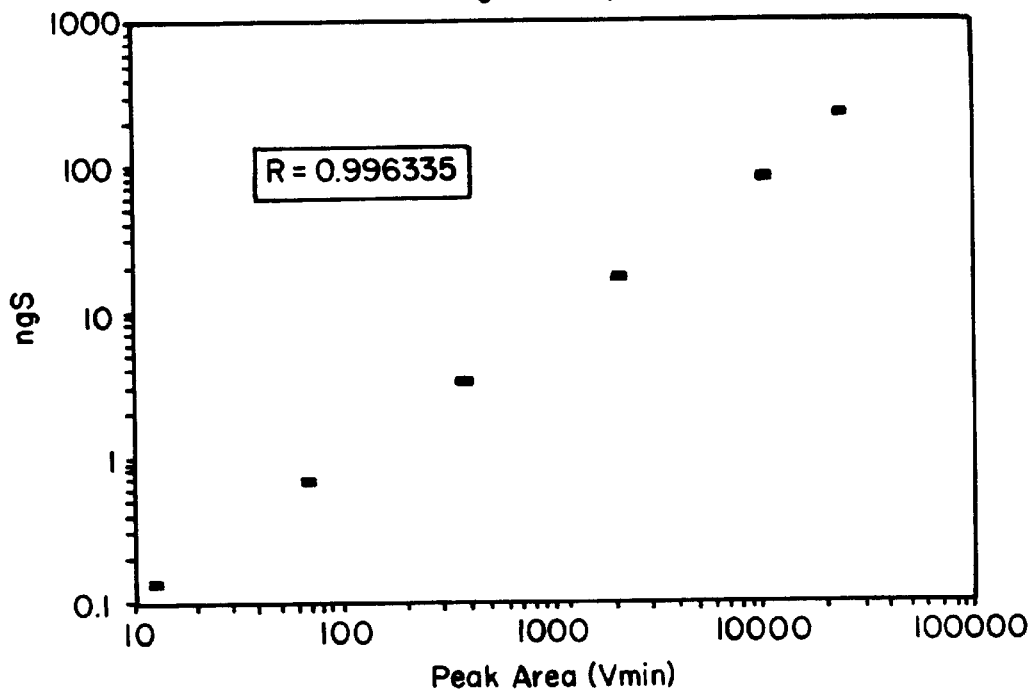
FIG. 7 are plots of relative response factors for the two sulfur standards 2-ethylthiophene and thianaphthene.
Figure 7:
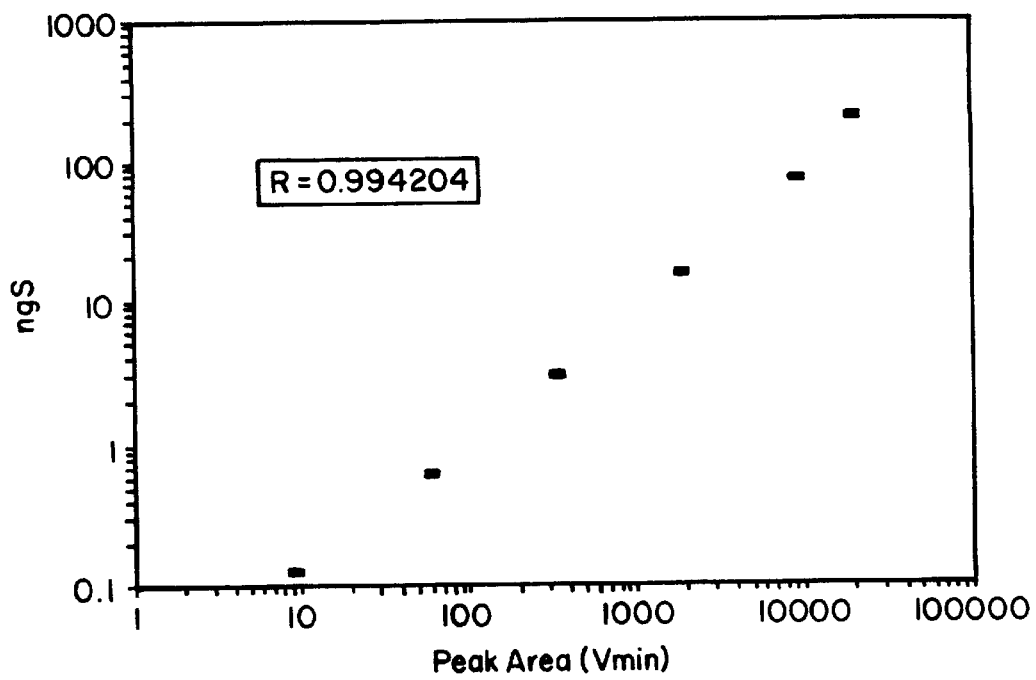
Figure 8:
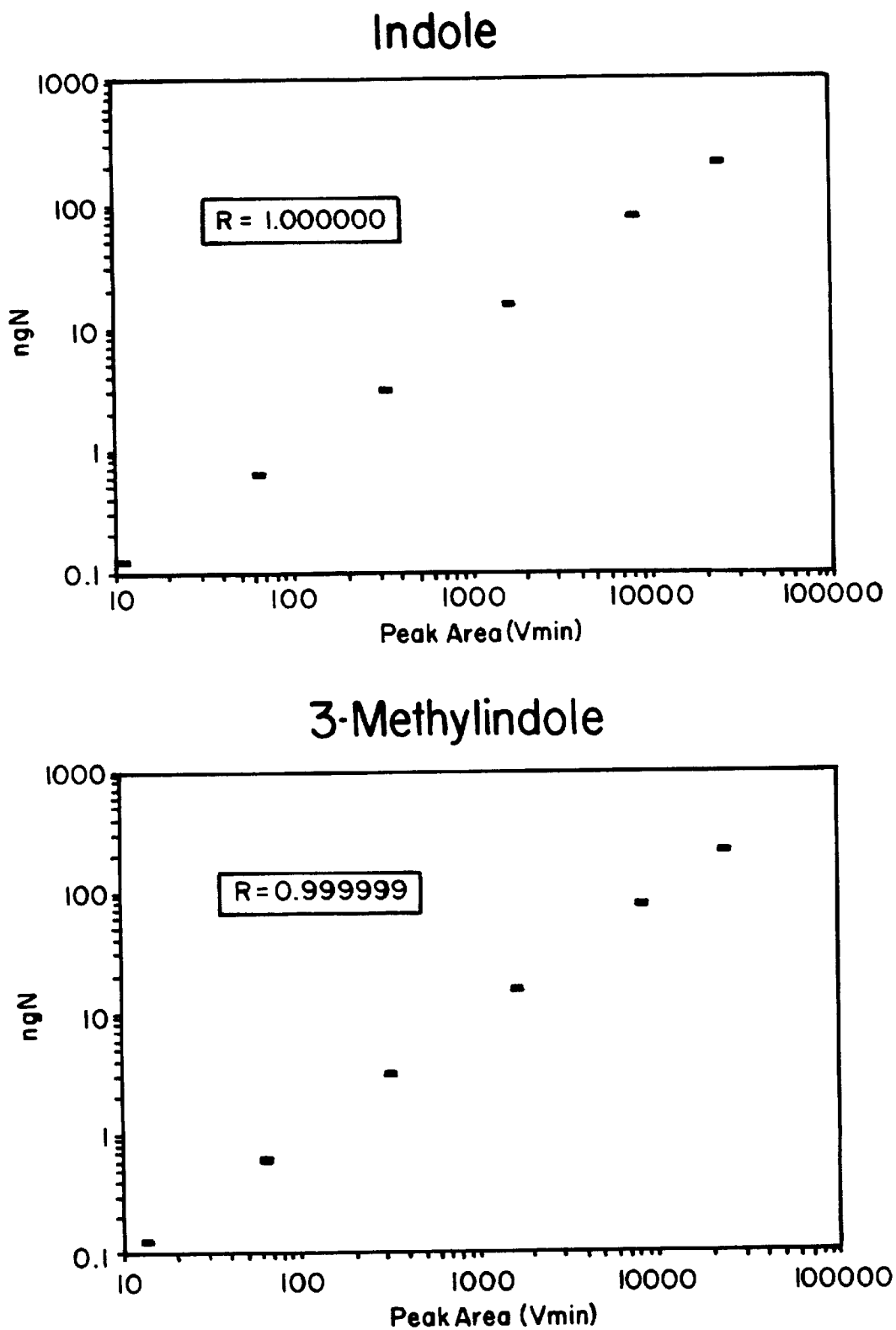
FIG. 8 are plots of relative response factors for the two nitrogen standards indole and 3-methylindole.

FIGS. 5 and 6 show chromatograms of the FID response from the GC and of the nitrogen CLND, and the sulfur CLSD of the present invention. FIGS. 7 and 8 show plots of the peak area verses nanograms of nitrogen or sulfur in the standards. From FIGS. 7 and 8, it can be seen that the apparatus of this invention gives nearly linear response over a wide concentration range for both nitrogen and sulfur.

After confirming that the apparatus 10 including the chamber 120 with its two sub-chambers 122 and 124 and associated detectors gave near linear responses to sulfur and nitrogen over a broad concentration range, compounds containing both sulfur and nitrogen or complex mixtures containing nitrogen, sulfur and nitrogen/sulfur compounds were analyzed. The compounds analyzed included thiamorpholine which has one sulfur and one nitrogen atom, heavy diesel, middle distillate, and regular gasoline.

Figure 9:
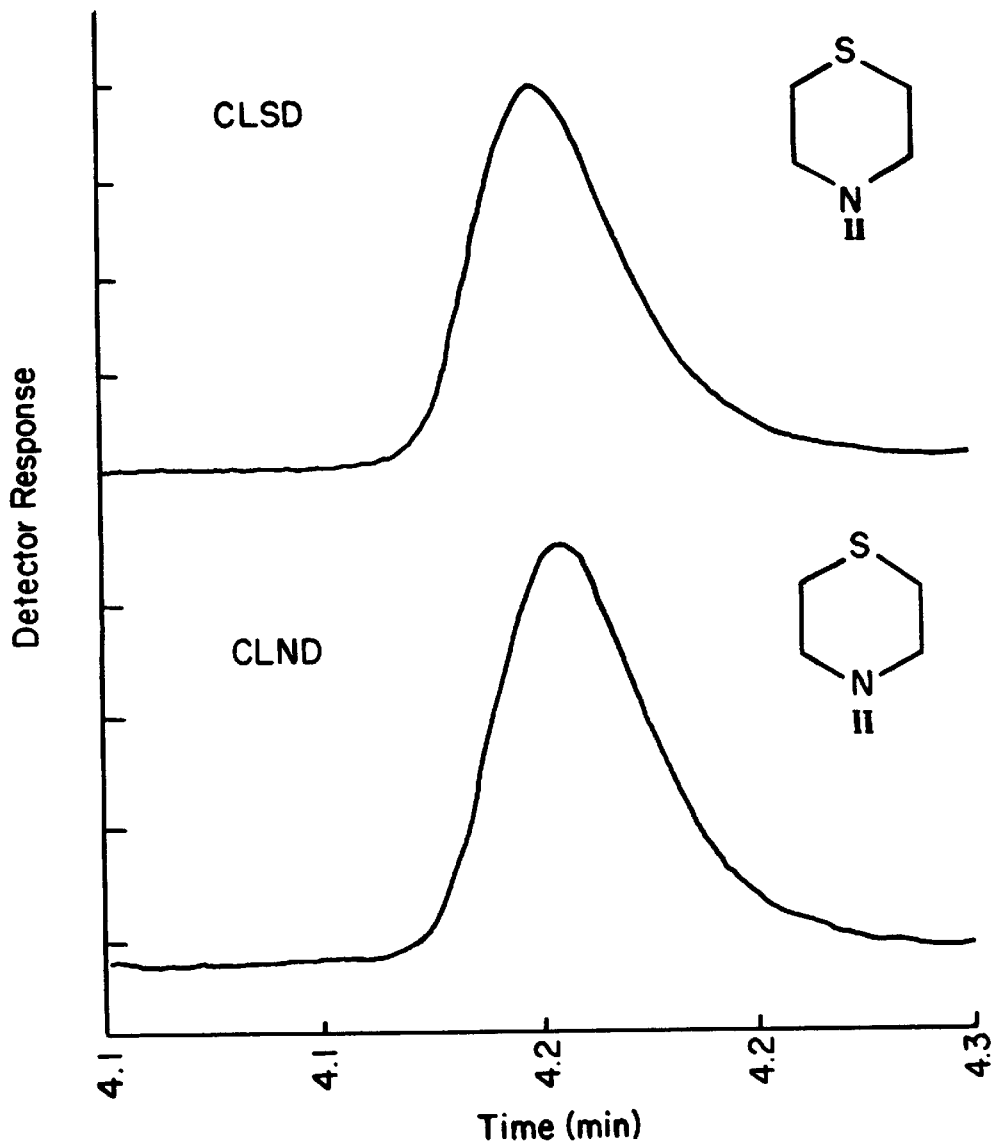
FIG. 9 is a set of simultaneous chromatograms showing near simultaneous detection of nitrogen and sulfur chemiluminescence of thiamorpholine using the apparatus of the present invention.
Figure 10:
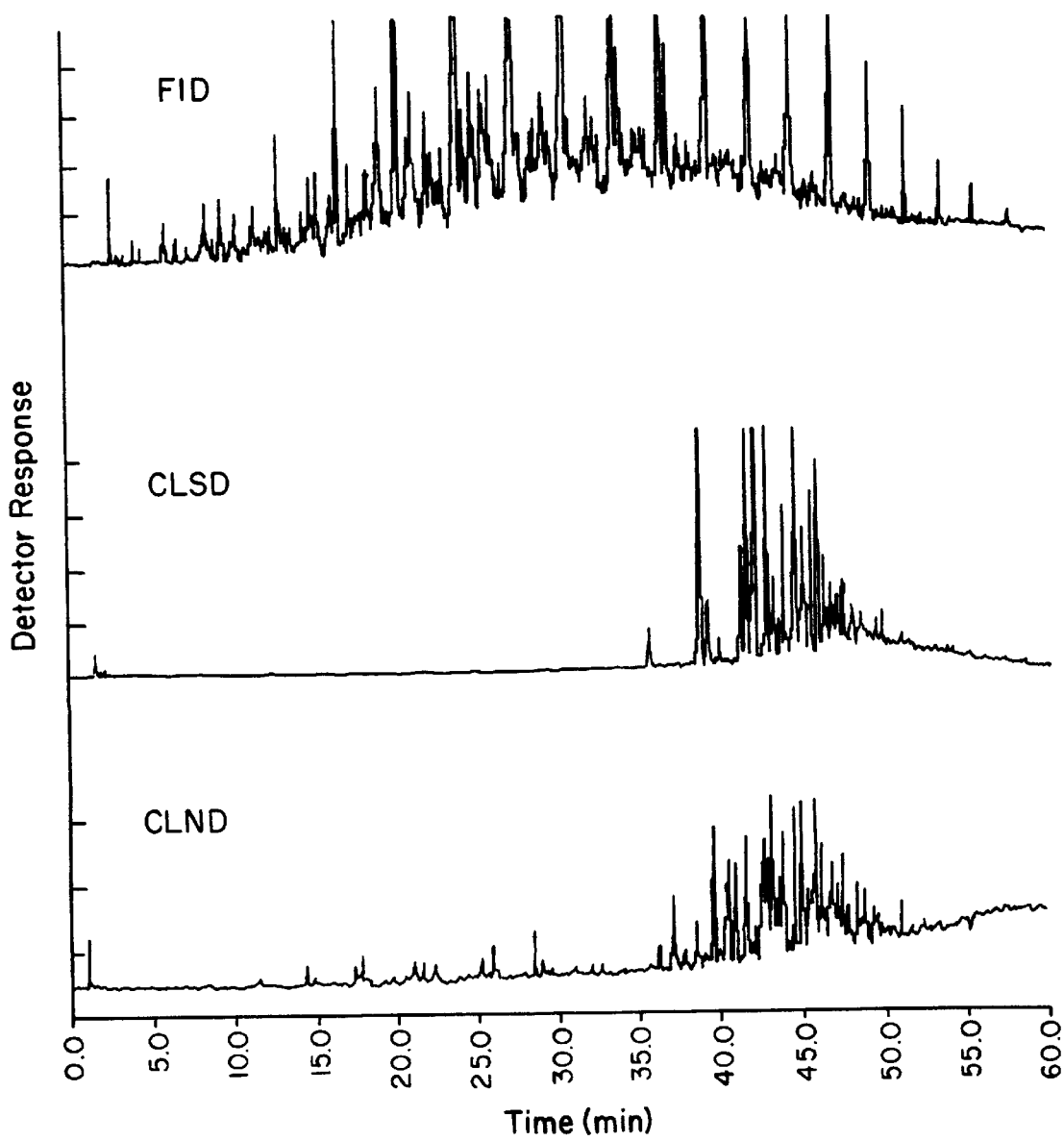
FIG. 10 is a set of simultaneous chromatograms of heavy diesel using the apparatus of the present invention.
Figure 11:
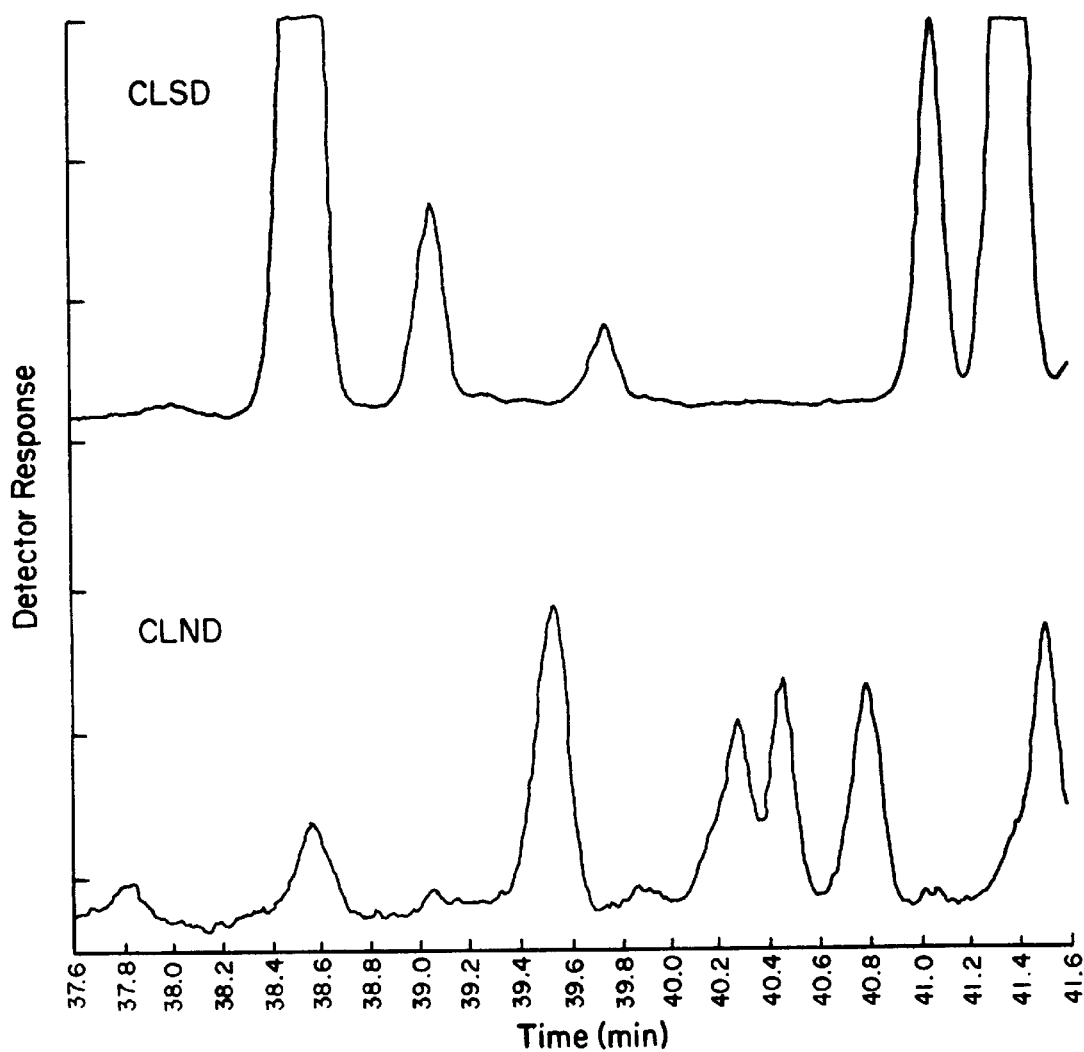
FIG. 11 expanded portions of the chromatograms of FIG. 10.
Figure 12:
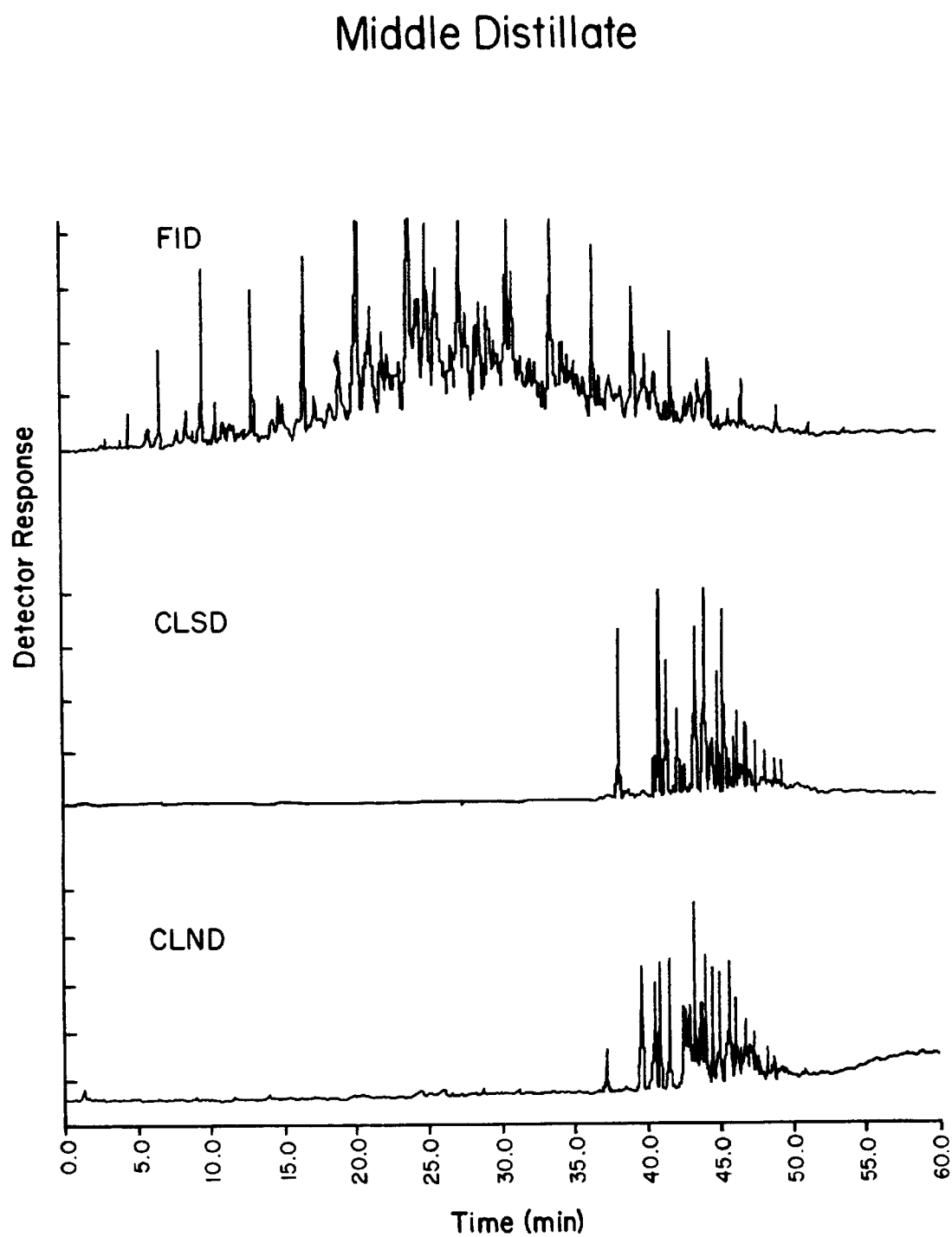
FIG. 12 is a set of simultaneous chromatograms of middle distillate using the apparatus of the present invention.
Figure 13:
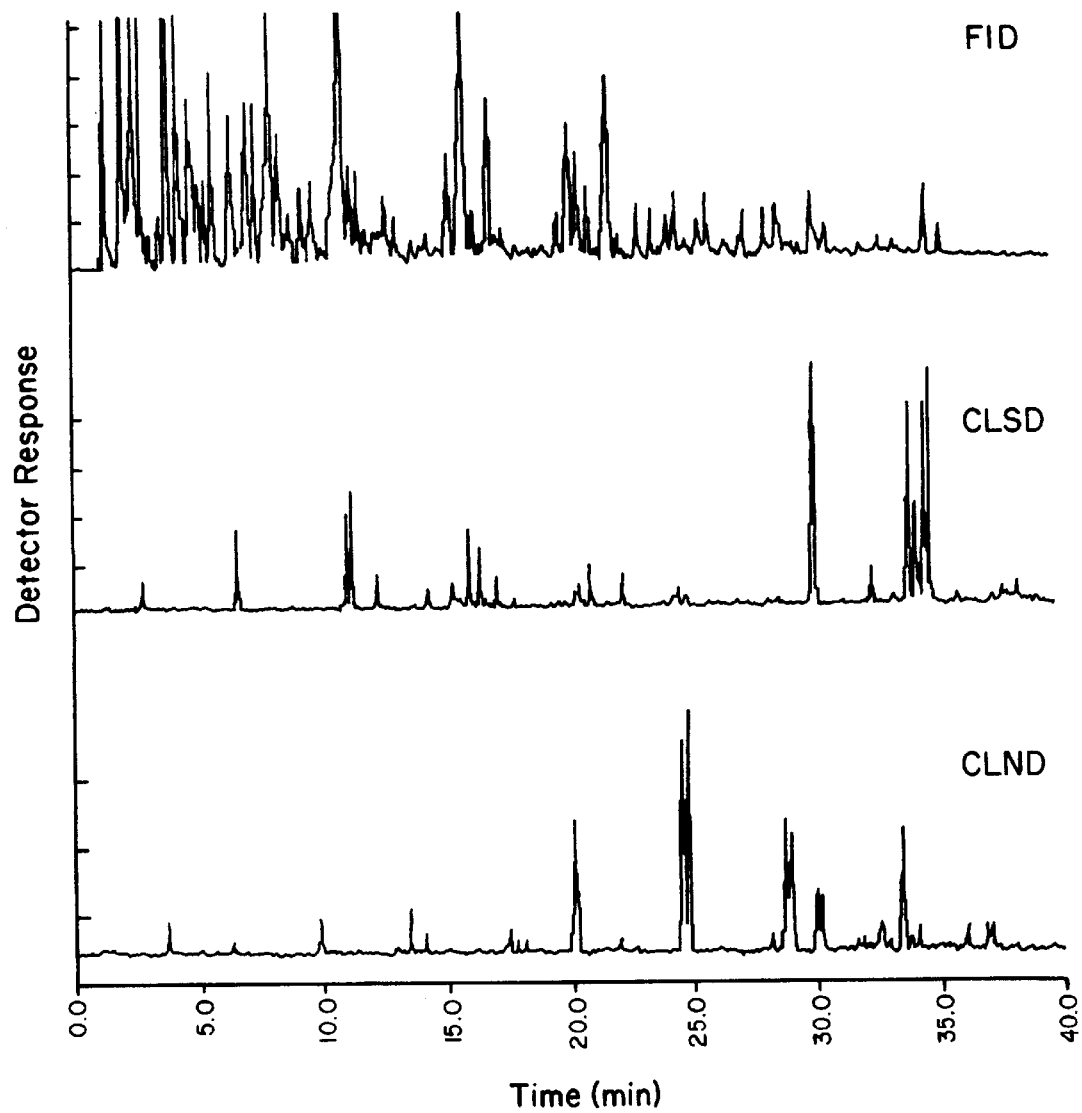
FIG. 13 is a set of simultaneous chromatograms of regular gasoline using the apparatus of the present invention.

FIGS. 9–13 show the chromatograms for each of these samples. FIG. 9 shows that the nitrogen and sulfur responses are near simultaneous for the analysis of thiamorpholine, while FIGS. 10–13 show the distribution of nitrogen, sulfur and nitrogen/sulfur compounds in heavy diesel, middle distillate and gasoline. It is interesting to note that heavy diesel and middle distillate have little sulfur and/or nitrogen containing compounds in the early part of the chromatograms, while gasoline has sulfur and nitrogen containing compounds distributed through out the entire profile. It is clear that this invention is an ideal analytical technique for near simultaneous detection of sulfur and nitrogen in individual molecular components or in complex molecular mixtures.

Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for detecting nitrogen and sulfur chemiluminescence comprising the steps of:

a. converting a portion of a nitrogen and sulfur content of a sample in a heated chamber in the presence of an oxidizing agent and a reducing agent into a detectable concentration of nitrogen and sulfur species capable of undergoing ozone induced chemiluminescence;

b. contacting the converted sample of step (a) with ozone to product meta-stable nitrogen and sulfur species in a single reaction/detection chamber including at least two sub-chambers, a nitrogen chemiluminescence detector associated with the first sub-chamber, and a sulfur chemiluminescence detector associated with the second sub-chamber, where the chamber is designed to inhibit light propagation between the sub-chambers;

c. detecting a nitrogen chemiluminescence derived from the meta-stable nitrogen species and a sulfur chemiluminescence derived from the meta-stable sulfur species in the reaction/detection chamber so that the nitrogen chemiluminescence does not substantially interference with detecting the sulfur chemiluminescence in the sulfur detector and the sulfur chemiluminescence does not substantially interfere with detecting the nitrogen chemiluminescence in the nitrogen detector.

2. The method of claim 1, wherein the converting step (a) includes the steps of:

i. oxidizing a portion of the nitrogen and sulfur content of the sample in an oxidation zone of the heated chamber in the presence of the oxidizing agent to generate nitrogen oxides and sulfur oxides; and ii. reducing a portion of the sulfur oxides in a reduction zone of the heated chamber in the presence of the reducing agent to generate reduced sulfur species capable of undergoing ozone induced chemiluminescence without reducing an amount of nitrogen oxides capable of undergoing ozone induced chemiluminescence below a detection limit of a nitrogen chemiluminescence detector.

3. The method of claim 1, wherein the oxidizing agent is oxygen.

4. The method of claim 1, wherein the reducing agent is hydrogen.

5. The method of claim 1, wherein the heated chamber is an open flame.

6. The method of clam 1, wherein the heated chamber is a furnace.

7. The method of claim 2, wherein the heated chamber is a furnace including an oxidative zone followed by a reductive zone.

8. The method of claim 7, wherein the furnace has an outer tube and an inner tube, where the inner tube extends down an interior of the outer tube from a first end to about a mid point of the outer tube and where an interior of the inner tube is the oxidation zone and a portion of the interior of the outer tube through which the inner tube does not extend is the reduction zone.

9. The method of claim 2, wherein the heated chamber includes an oxidation furnace and a reduction furnace where a portion of an effluent from the oxidation furnace is an influent of the reduction furnace.

10. The method of claim 1, wherein the reaction/detection chamber includes a first sub-chamber, an air permeable, light barrier and a second sub-chamber where the nitrogen detector is associated with the first sub-chamber and the sulfur detector is associated with the second sub-chamber.

11. The method of claim 10, wherein the light barrier is a perforated disk where the perforations are designed to prevent an interfering amount of light to propagate between the sub-chambers.

12. The method of claim 10, wherein the light barrier is a tube are designed to prevent an interfering amount of light to propagate between the sub-chambers.

13. The method of claim 1, wherein the reaction/detection chamber comprises a U-shaped chamber including a first end having the nitrogen detector associated therewith the, a second end having the sulfur detector associated therewith, and a distance adjusting device for shortening or lengthening the gas travel distance between the first and second end so that light derived from sulfur chemiluminescence does not substantially interference with the detection of nitrogen chemiluminescence by the nitrogen detector associated with the first end and that light derived from nitrogen chemiluminescence does not substantially interference with the detection of sulfur chemiluminescence by the sulfur detector associated with the second end.

14. The method of claim 13, wherein the device for adjusting is a U-shaped sliding member associated with a central part of the U-shaped chamber, where the sliding action maintains the light tight nature of the chamber.

* * * * *